US008580255B2

(12) United States Patent
Heffernan et al.

(10) Patent No.: US 8,580,255 B2
(45) Date of Patent: Nov. 12, 2013

(54) METHOD FOR THE TREATMENT OF RHEUMATOID ARTHRITIS USING A TLR2 ANTAGONISTIC ANTIBODY

(75) Inventors: Mark Heffernan, Dublin (IE); Luke O'Neill, Dublin (IE); Peter McGuirk, Dublin (IE); Brian Keogh, Dublin (IE); Christopher Locher, Lexington, MA (US)

(73) Assignee: OPSONA Therapeutics Ltd, Dublin (IE)

( * ) Notice: Subject to any disclaimer, the term of this patent is extended or adjusted under 35 U.S.C. 154(b) by 0 days.

(21) Appl. No.: 12/666,442

(22) PCT Filed: Jun. 27, 2008

(86) PCT No.: PCT/EP2008/058339
§ 371 (c)(1),
(2), (4) Date: Jun. 8, 2010

(87) PCT Pub. No.: WO2009/000929
PCT Pub. Date: Dec. 31, 2008

(65) Prior Publication Data
US 2010/0247527 A1  Sep. 30, 2010

Related U.S. Application Data

(60) Provisional application No. 61/038,372, filed on Mar. 20, 2008.

(30) Foreign Application Priority Data

Jun. 28, 2007  (IE) ..................................... 2007/0468
Mar. 20, 2008  (IE) ..................................... 2008/0209

(51) Int. Cl.
*A61K 39/395*  (2006.01)
*A61P 37/04*  (2006.01)
*C12N 5/07*  (2010.01)

(52) U.S. Cl.
USPC .................. 424/130.1; 424/133.1; 424/144.1; 424/158.1; 424/173.1; 435/375; 514/16.6

(58) Field of Classification Search
None
See application file for complete search history.

(56) References Cited

U.S. PATENT DOCUMENTS 7,202,234 B2 *  4/2007  Chow et al. ..................... 514/80
2005/0074823 A1 *  4/2005  Kurt-Jones et al. ............. 435/7.2
2006/0165686 A1 *  7/2006  Elson et al. .................. 424/143.1

FOREIGN PATENT DOCUMENTS

| WO | WO 01/36488 A1 | 5/2001 |
|----|----------------|--------|
| WO | WO 2005/028509 A1 | 3/2005 |
| WO | WO-2005/079419 A2 | 9/2005 |
| WO | WO 2006/077471 A2 | 7/2006 |
| WO | WO 2006/088833 A2 | 8/2006 |
| WO | WO 2008/132516 A1 | 11/2008 |

OTHER PUBLICATIONS

Frasnelli et al, Arthritis Research Therapy, 2005, vol. 7, pp. R370-R379.*
Nozaki et al, Arthritis & Rheumatism, Sep. 2007, vol. 56, No. 9, pp. 2875-2885.*
Meng et al, The Journal of Clinical Investigation, 2004, vol. 113, No. 10, pp. 1473-1481.*
Abdollahi-Roodsaz et al., Stimulation of TLR2 and TLR4 differentially skews the balance of T cells in a mouse model of arthritis. J Clin Invest. Jan. 2008;118(1):205-16.
Cho et al., Toll-like receptor 2 ligand mediates the upregulation of angiogenic factor, vascular endothelial growth factor and interleukin-8/CXCL8 in human rheumatoid synovial fibroblasts. Immunol Lett. Feb. 15, 2007;108(2):121-8. Epub Dec. 11, 2006.
Iwahashi et al., Expression of Toll-like receptor 2 on CD16+ blood monocytes and synovial tissue macrophages in rheumatoid arthritis. Arthritis Rheum. May 2004;50(5):1457-67.
Kyburz et al., Bacterial peptidoglycans but not CpG oligodeoxynucleotides activate synovial fibroblasts by toll-like receptor signaling. Arthritis Rheum. Mar. 2003;48(3):642-50.
Arslan et al., *Myocardial Ischemia/Reperfusion Injury Is Mediated by Leukocytic Toll-Like Receptor-2 and Reduced by Systemic Administration of a Novel Anti-Toll-Like Receptor-2 Antibody*, Circulation AHA, 2010, 121:80-90.
Nic An Ultaigh et al., *Blockade of Toll-like receptor 2 prevents spontaneous cytokine release from rheumatoid arthritis ex vivo synovial explant cultures*, Arthritis Research & Therapy, 2011, 13:R33.
Abdollahi-Roodsaz, Shahia et al., *Local Interleukin-1-Driven Joint Pathology Is Dependent on Toll-Like Receptor 4 Activation*, The American Journal of Pathology, vol. 175, No. 5, pp. 2004-2013 (2009).
Blom, A. B. et al., Abstract, *Toll Like Receptor 2 and 4 Do Not Aggravate Joint Pathology in Osteoarthritis*, Podium Presentations, Osteoarthritis and Cartilage vol. 14, Supplement B, pp. S20-S21, Dec. 10, 2006, Prague, Czech Republic.
Sanchez, E. et al., *Polymorphisms of toll-like receptor 2 and 4 genes in rheumatoid arthritis and systemic lupus erythematosus*, Tissue Antigens 2004; 63:54-57.

* cited by examiner

*Primary Examiner* — Bridget E Bunner
*Assistant Examiner* — Fozia Hamud
(74) *Attorney, Agent, or Firm* — Wolf, Greenfield & Sacks, P.C.

(57) ABSTRACT

The present invention provides compositions and methods for the treatment of autoimmune diseases, in particular rheumatoid arthritis. Compounds which function as antagonists of Toll-like Receptor 2 are shown to suppress the immune response which result in the onset and progression of autoimmune disease. In particular monoclonal antibodies which have a binding specificity to Toll-like receptor 2 are disclosed for use in methods for the treatment and/or prophylaxis of autoimmune disease.

13 Claims, 22 Drawing Sheets

(a)
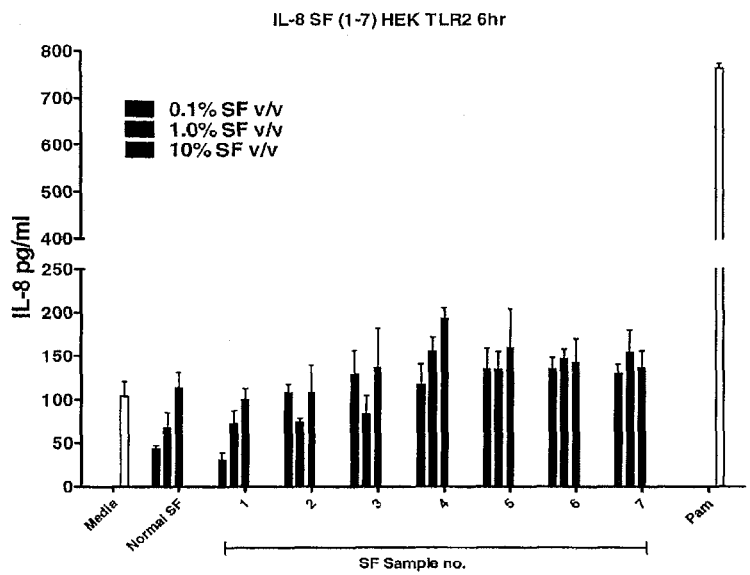
(b)
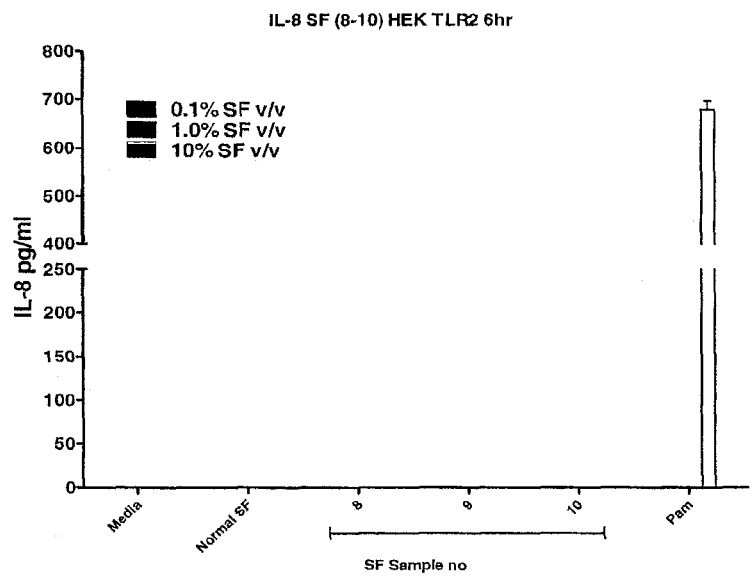
Figure 1(a) and (b) IL-8 responses from 293 HEK-TLR2 cells stimulated with putative synovial fluid samples after 6 hours.

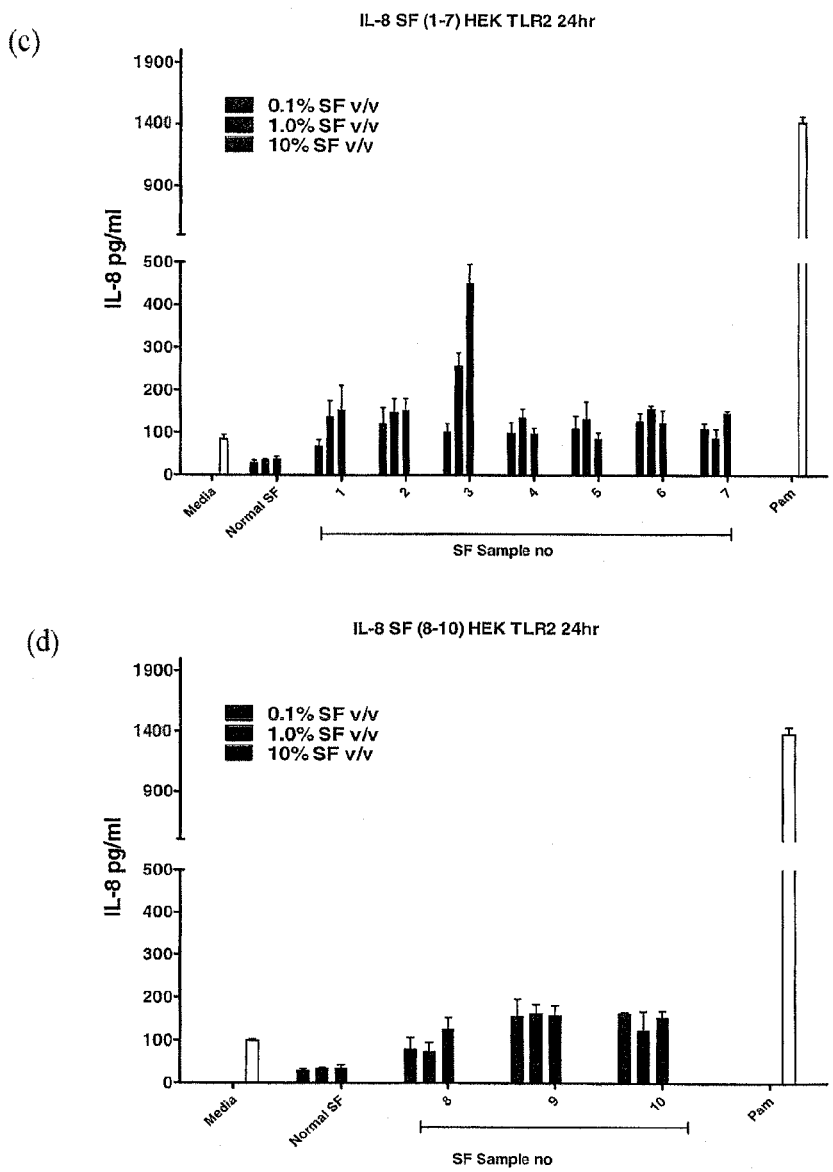
Figure 1(c) and (d) IL-8 responses from 293 HEK-TLR2 cells stimulated with putative synovial fluid samples after 24 hours.

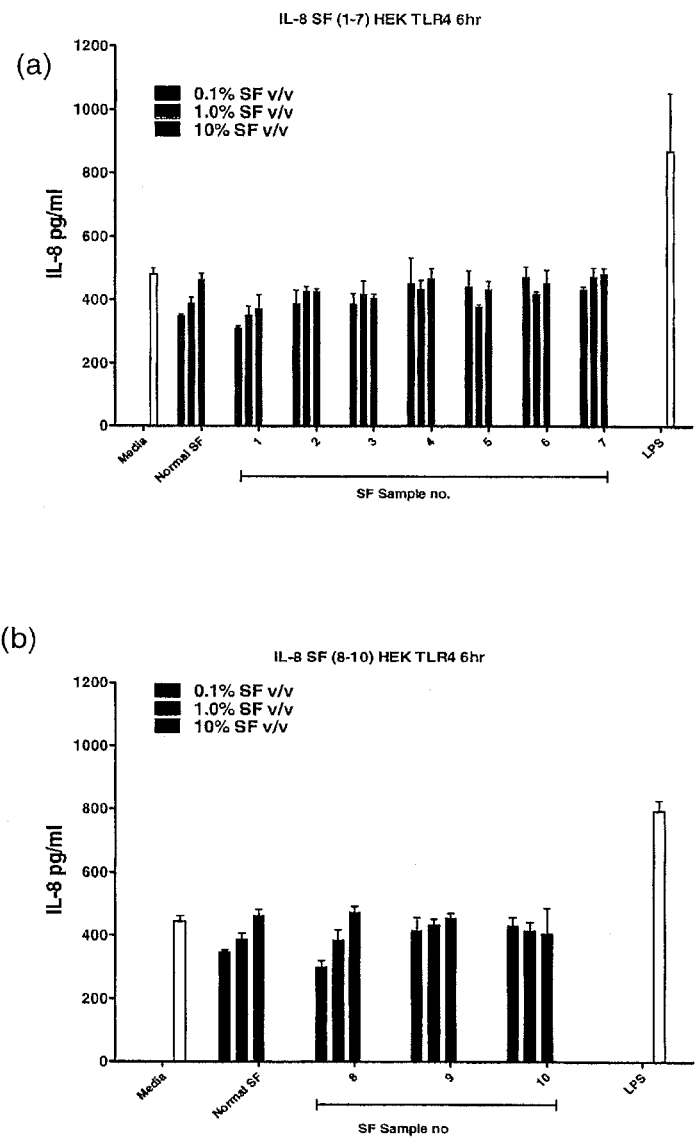
Figure 2 (a) and (b) - IL-8 responses from 293 HEK-TLR4 cells stimulated with putative synovial fluid samples.

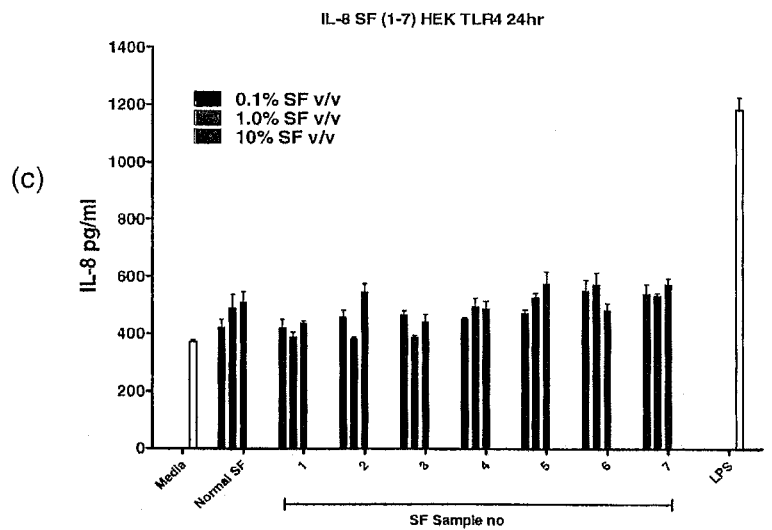
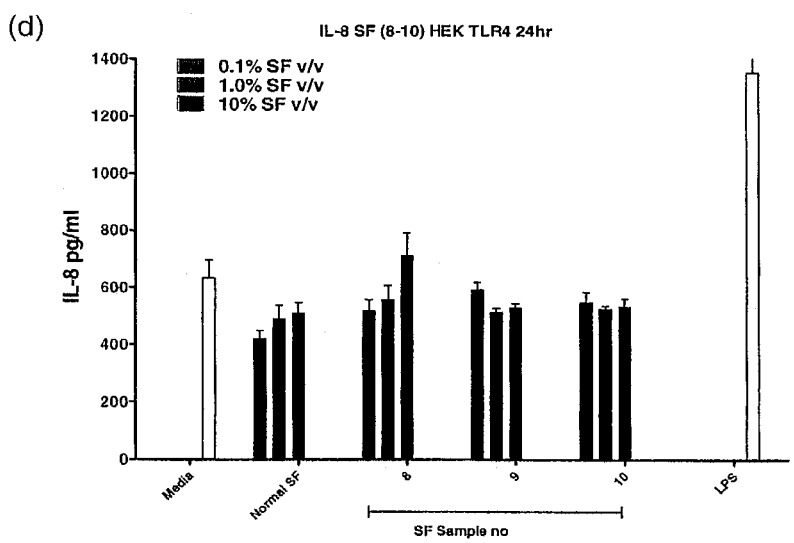
Figure 2 (c) and (d) - IL-8 responses from 293 HEK-TLR4 cells stimulated with putative synovial fluid samples.

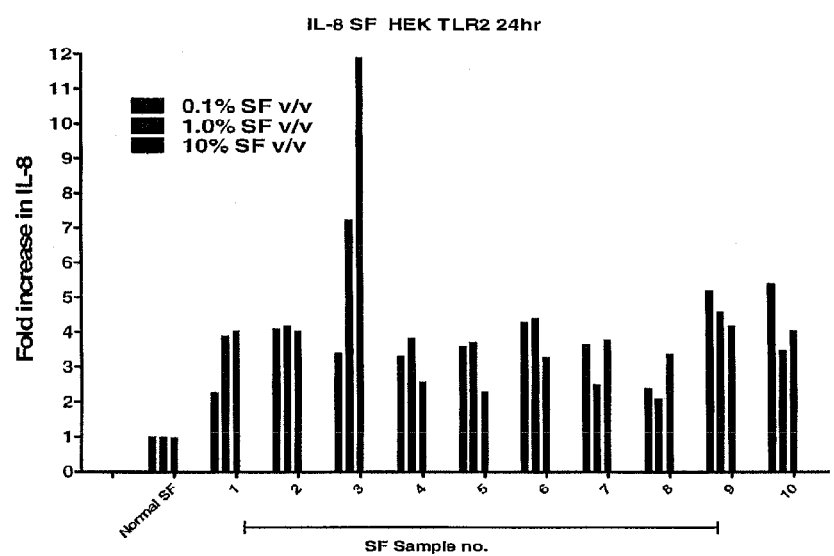
Figure 3. Fold increase in IL-8 from putative SF samples over normal synovial fluid in HEK-TLR-2 cells stimulated for 24hrs.

```
  1 mphtlwmvwv lgviislske essnqaslsc drngickgss gslnsipsgl teavksldls
 61 nnrityisns dlqrcvnlqa lvltsngint ieedsfsslg slehldlsyn ylsnlssswf
121 kplssltfln llgnpyktlg etslfshltk lqilrvgnmd tftkiqrkdf agltfleele
181 idasdlqsye pkslksiqnv shlilhmkqh illleifvdv tssveclelr dtdldtfhfs
241 elstgetnsl ikkftfrnvk itdeslfqvm kllnqisgll elefddctln gvgnfrasdn
301 drvidpgkve tltirrlhip rfylfydlst lysltervkr itvenskvfl vpcllsqhlk
361 sleyldlsen lmveeylkns acedawpslq tlilrqnhla slektgetll tlknltnidi
421 sknsfhsmpe tcqwpekmky lnlsstrihs vtgcipktle ildvsnnnln lfslnlpqlk
481 elyisrnklm tlpdasllpm llvlkisrna ittfskeqld sfhtlktlea ggnnficsce
541 flsftqeqqa lakvlidwpa nylcdspshv rgqqvqdvrl svsechrtal vsgmccalfl
601 lilltgvlch rfhglwymkm mwawlqakrk prkapsrnic ydafvsyser daywvenlmv
661 qelenfnppf klclhkrdfi pgkwiidnii dsiekshktv fvlsenfvks ewckyeldfs
721 hfrlfeennd aailillepi ekkaipqrfc klrkimntkt ylewpmdeaq regfwvnlra
781 aiks
```

Figure 4. Amino acid sequence of human Toll-like Receptor 2 (SEQ ID NO:1)

```
  1 mlralwlfwi lvaitvlfsk rcsaqeslsc dasgvcdgrs rsftsipsgl taamksldls
 61 fnkityighg dlracanlqv lmlkssrint iegdafyslg slehldlsdn hlsslssswf
121 gplsslkyln lmgnpyqtlg vtslfpnltn lqtlrignve tfseirridf agltslnele
181 ikalslrnyq sqslksirdi hhltlhlses aflleifadi lssvrylelr dtnlarfqfs
241 plpvdevssp mkklafrgsv ltdesfnell kllryilels evefddctln glgdfnpses
301 dvvselgkve tvtirrlhip qfylfydlst vysllekvkr itvenskvfl vpcsfsqhlk
361 slefldlsen lmveeylkns ackgawpslq tlvlsqnhlr smqktgeill tlknltsldi
421 srntfhpmpd scqwpekmrf lnlsstgirv vktcipqtle vldvsnnnld sfslflprlq
481 elyisrnklk tlpdaslfpv llvmkirena vstfskdqlg sfpkletlea gdnhfvcsce
541 llsftmetpa laqilvdwpd sylcdspprl hghrlqdarp svlechqaal vsgvccalll
601 lillvgalch hfhglwylrm mwawlqakrk pkkapcrdvc ydafvsyseq dshwvenlmv
661 qqlensdppf klclhkrdfv pgkwiidnii dsiekshktv fvlsenfvrs ewckyeldfs
721 hfrlfdennd aailvllepi erkaipqrfc klrkimntkt ylewpldegq qevfwvnlrt
781 aiks
```

Figure 5. Amino acid sequence of murine Toll-like Receptor 2 (SEQ ID NO:2)

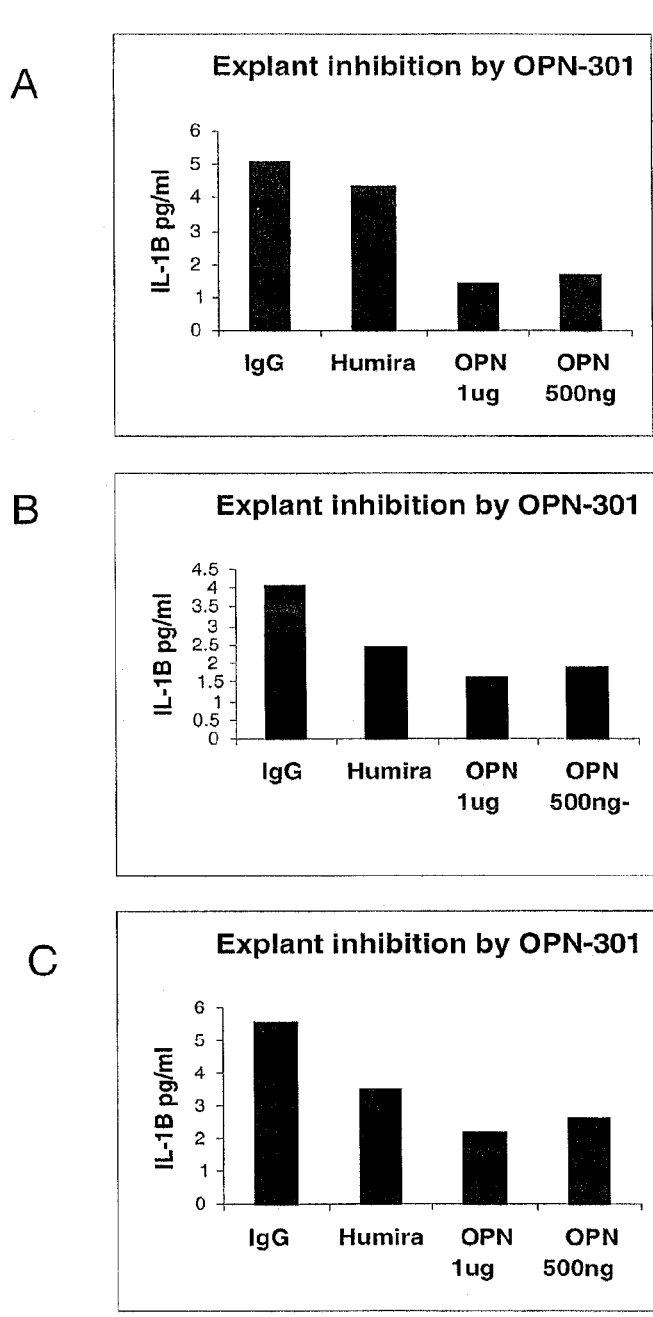
Figure 6. IL-1beta cytokine expression

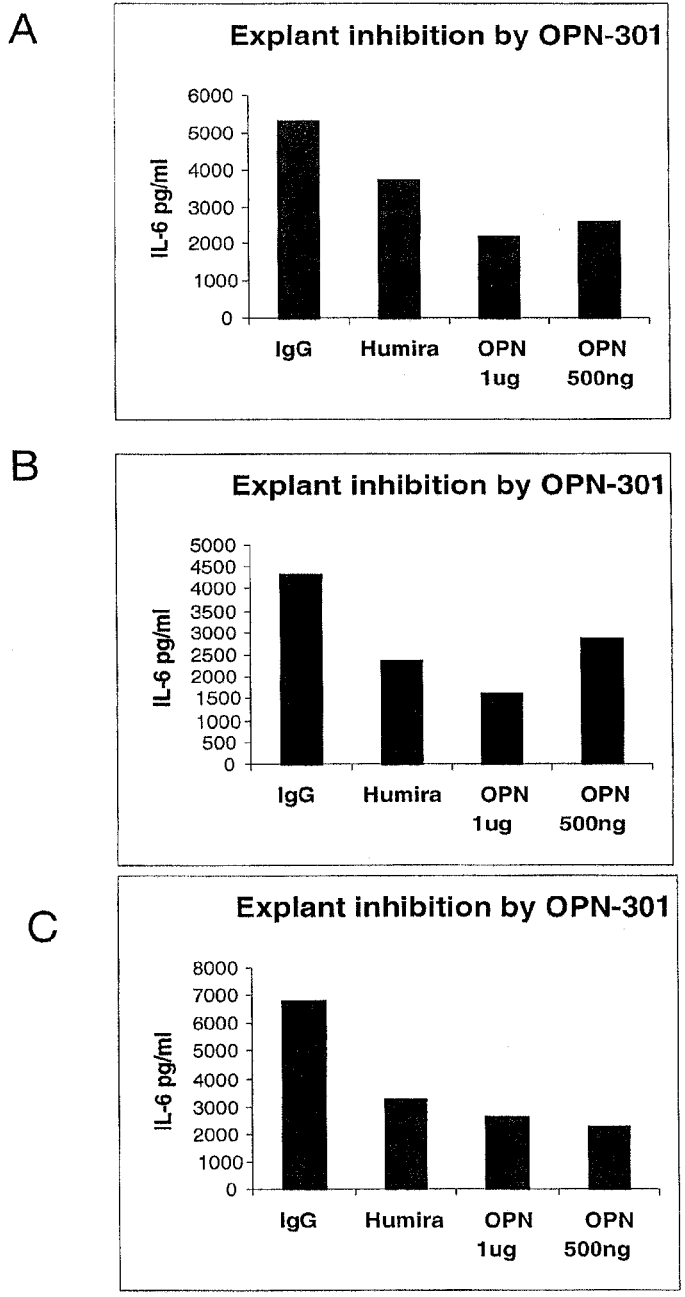
Figure 7. IL-6 cytokine expression

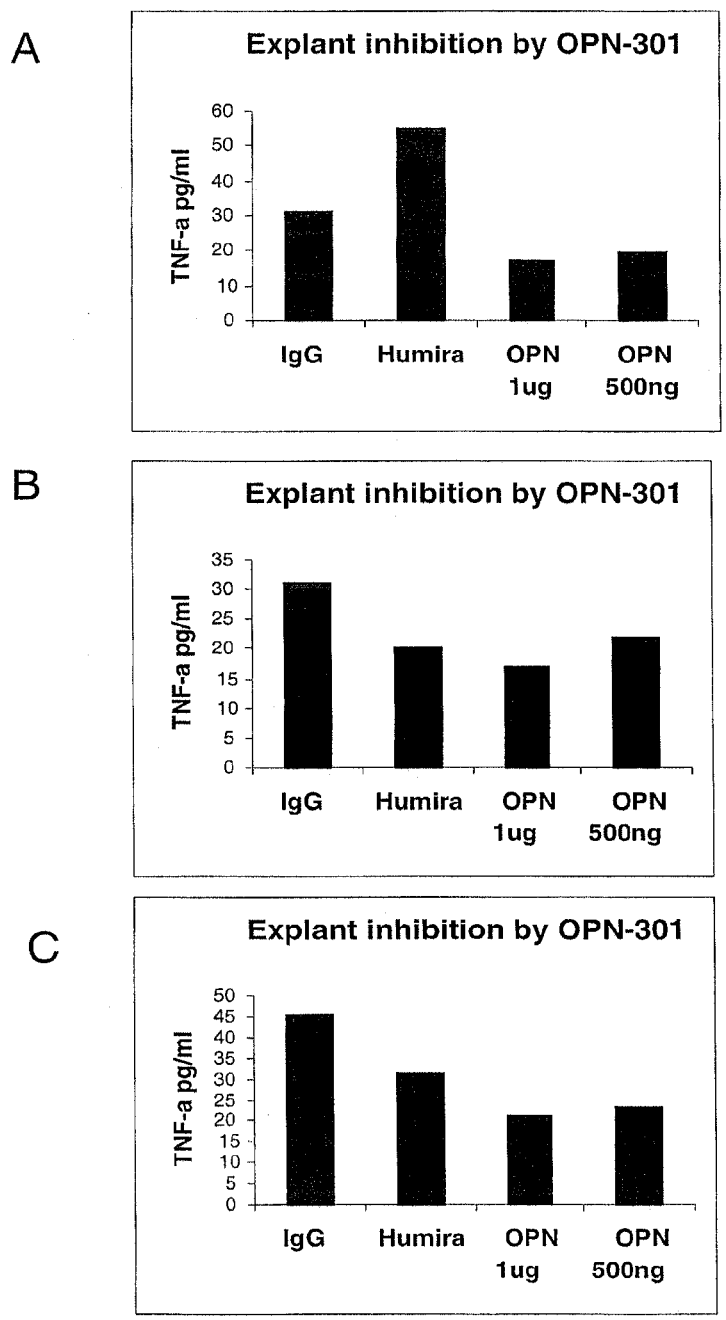
Figure 8. TNF-alpha cytokine expression

A 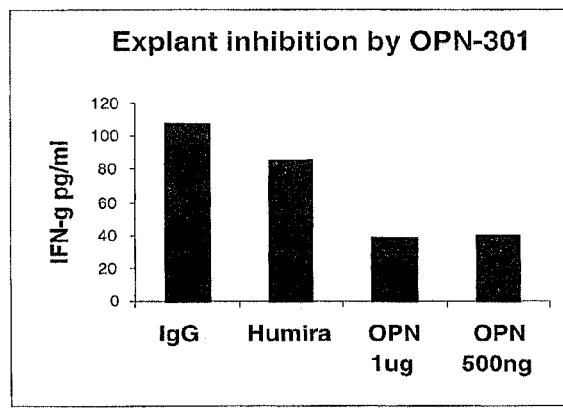
B 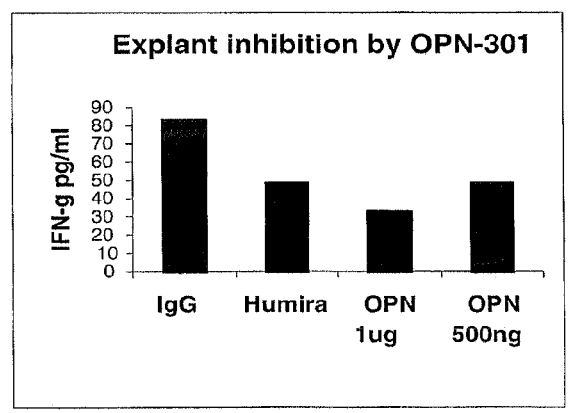
C 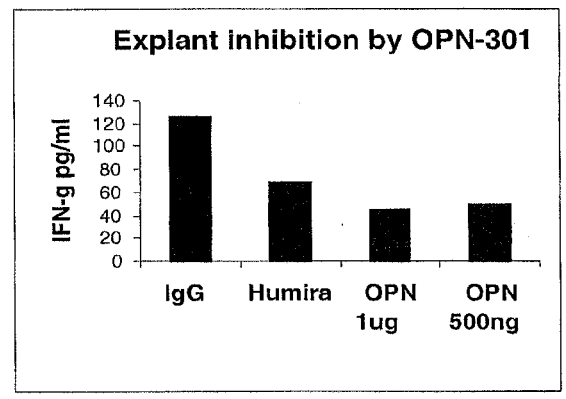
Figure 9. IFN-gamma cytokine expression

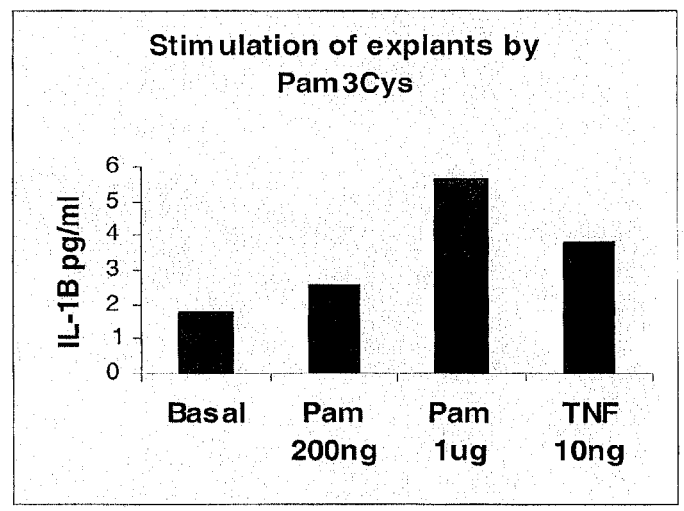
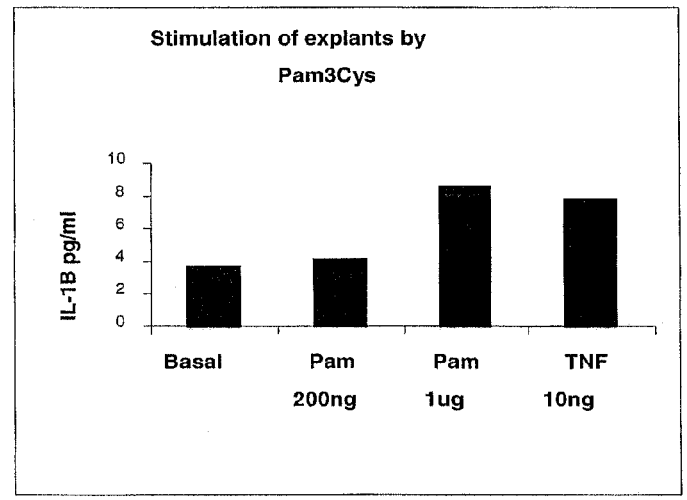
Figure 10. IL-1beta cytokine expression following administration of a TLR2 agonist

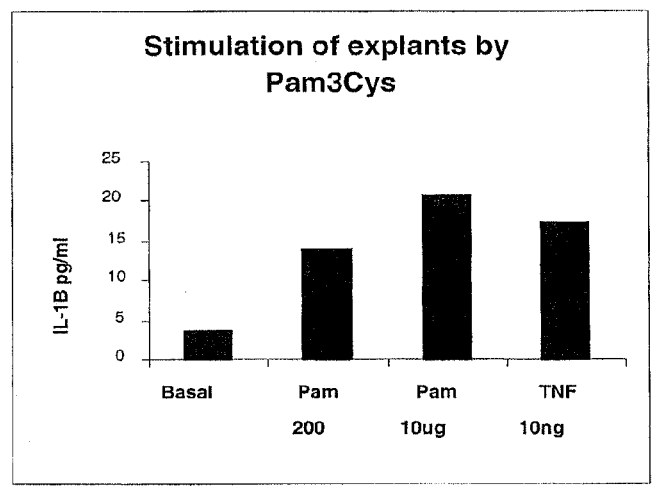
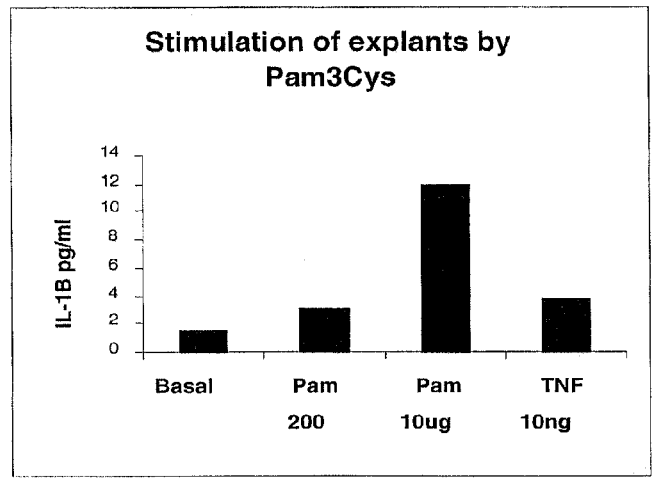
Figure 10 – C, D

A
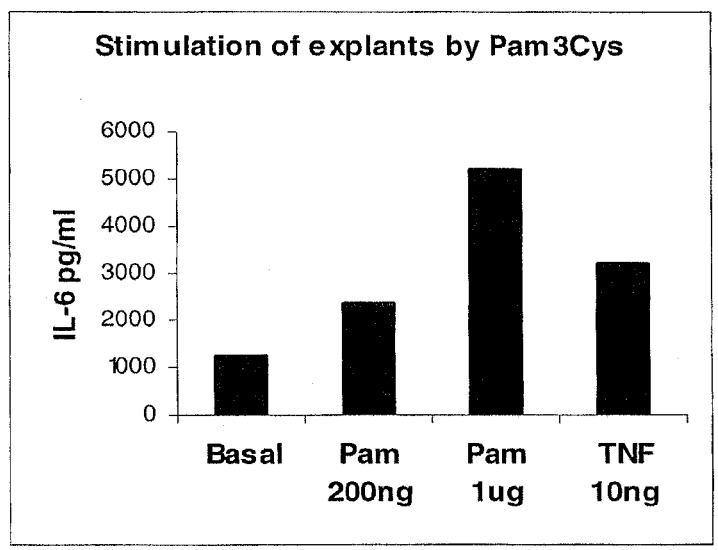
B
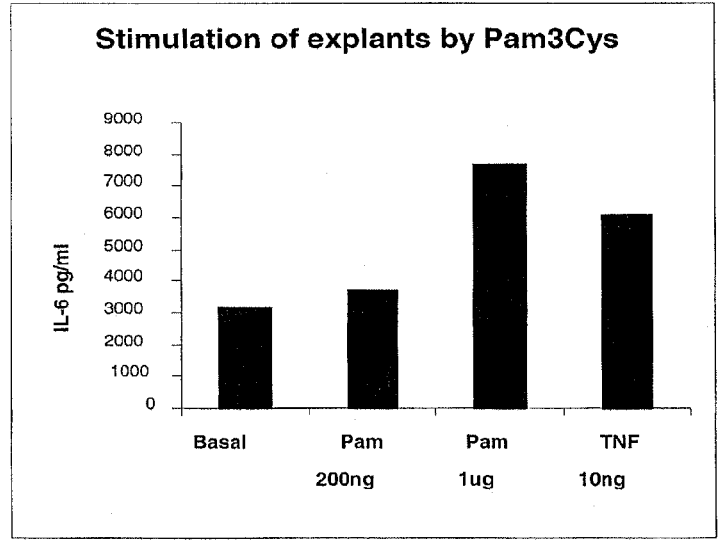
Figure 11. IL-6 cytokine expression following administration of a TLR2 agonist

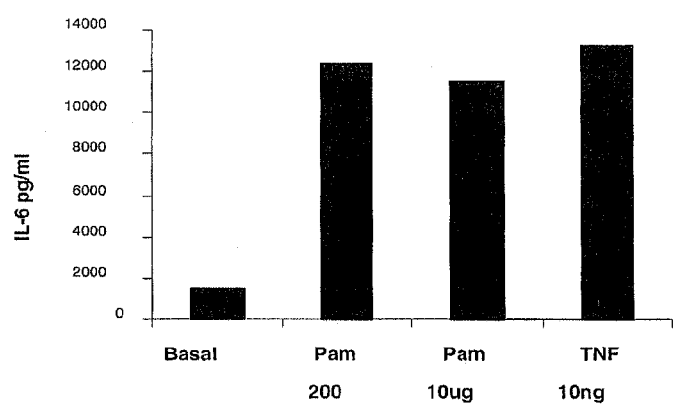
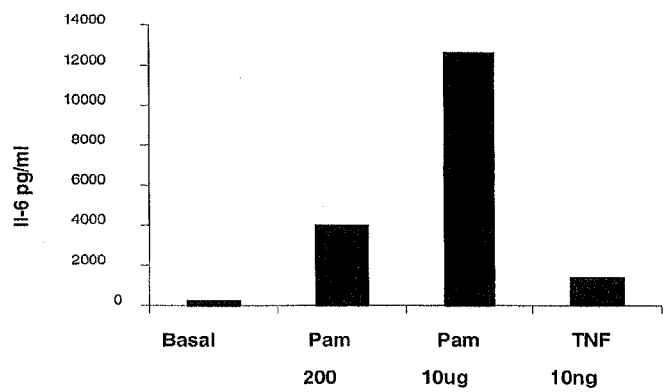
Figure 11 – C, D

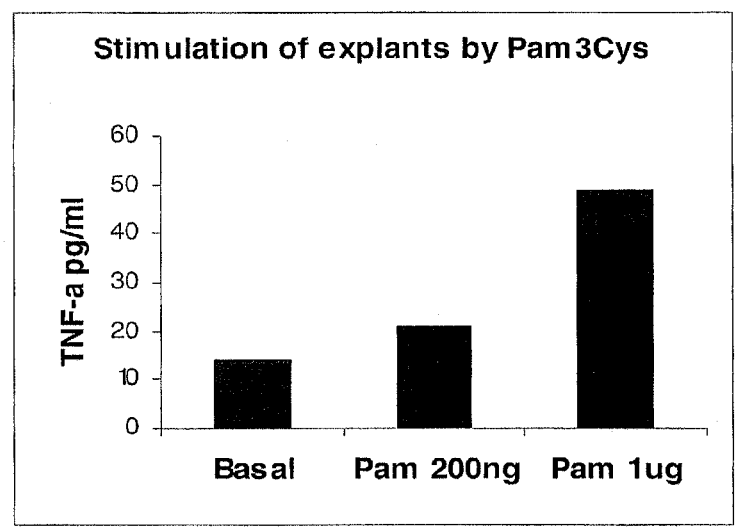
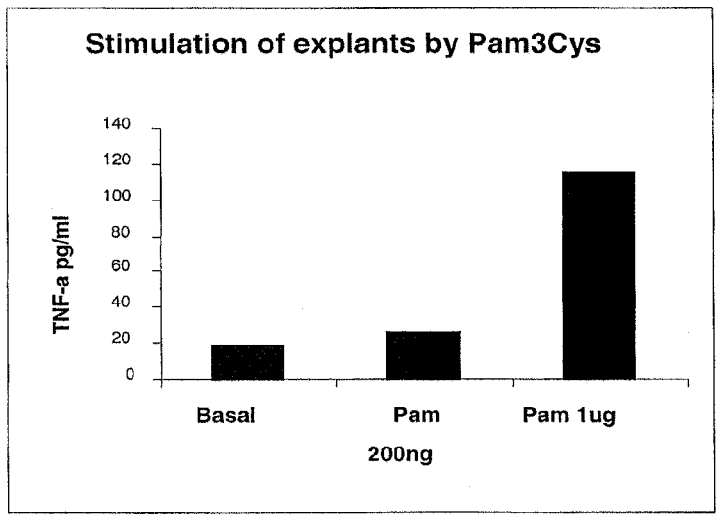
Figure 12. TNF-alpha cytokine expression following administration of a TLR2 agonist

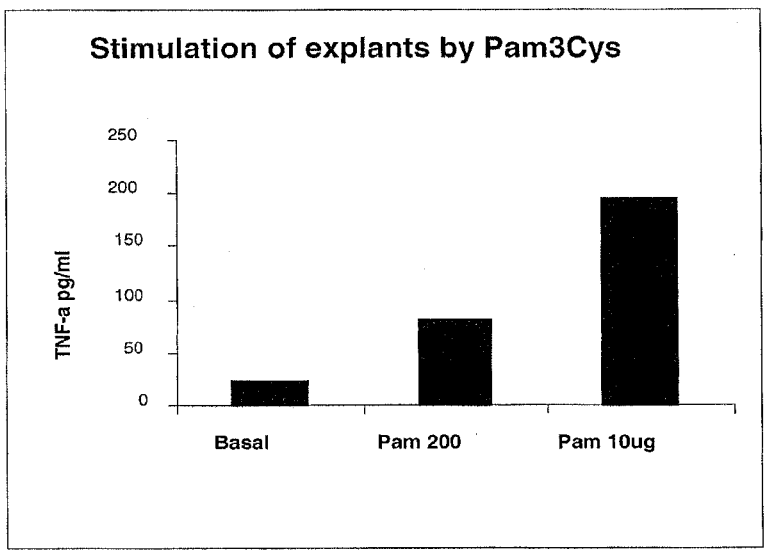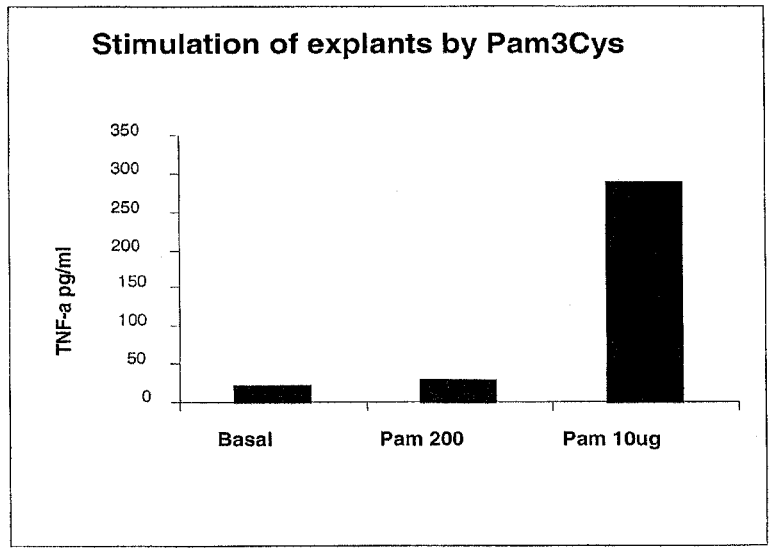
Figure 12 – C, D

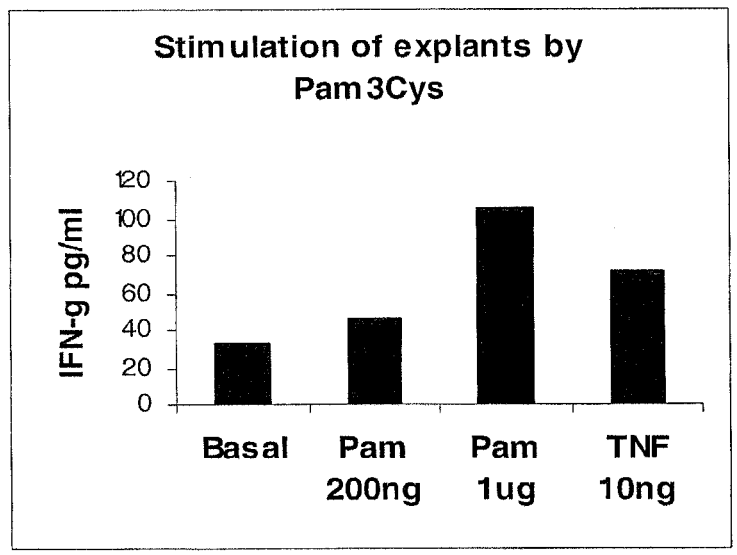
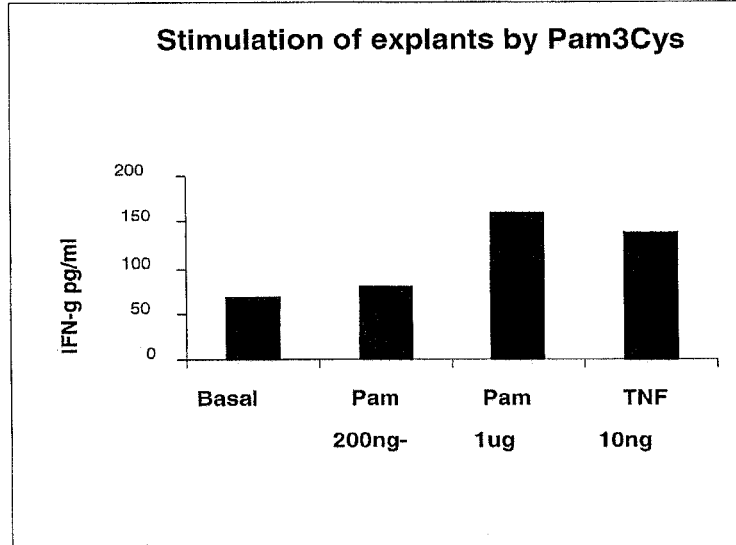
Figure 13. IFN-gamma cytokine expression following administration of a TLR2 agonist

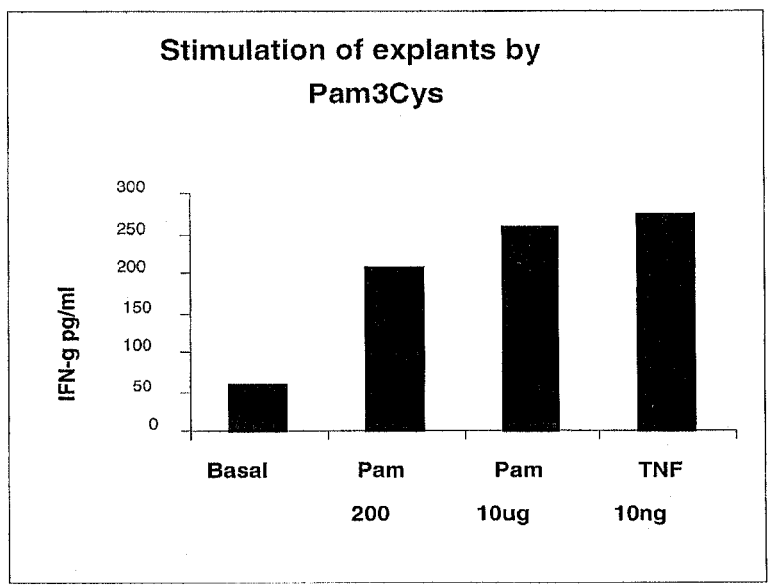
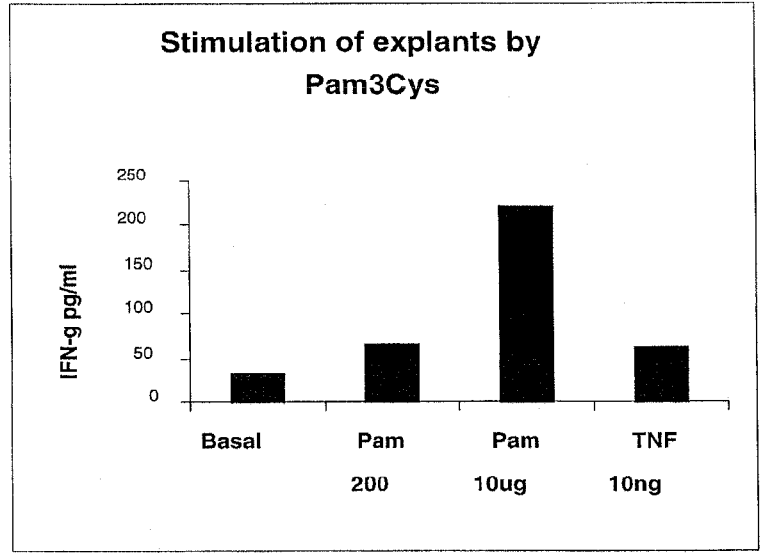
Figure 13 – C, D

METHOD FOR THE TREATMENT OF RHEUMATOID ARTHRITIS USING A TLR2 ANTAGONISTIC ANTIBODY

CROSS REFERENCE TO RELATED APPLICATIONS

This application is a national stage filing under 35 U.S.C. §371 of international application PCT/EP2008/058339, filed Jun. 27, 2008, which was published under PCT Article 21(2) in English, and which claims the benefit under 35 USC §119 (e) of U.S. Provisional Application No. 61/038,372, filed Mar. 20, 2008, and also Ireland Applications No. 2007/0468, filed Jun. 28, 2007, and No. 2008/0209 filed Mar. 20, 2008, the disclosures of all of which are incorporated by reference herein in their entirety.

FIELD OF THE INVENTION

The present invention relates to compounds and methods for the treatment of arthritis. In particular there is provided methods for the treatment and prophylaxis of rheumatoid arthritis which function by inhibiting the function and/or expression of Toll-like Receptor 2.

BACKGROUND TO THE INVENTION

Arthritis is a progressive, inflammatory autoimmune disease. The most prevalent form of arthritis is rheumatoid arthritis, a chronic inflammatory disorder which is characterised by inflammation of the joints. Although rheumatoid arthritis rarely leads to mortality, the associated symptoms of rheumatoid arthritis, which most typically include the loss of joint mobility, can cause a significant impairment to an individual's quality of life.

Rheumatoid arthritis (RA) is typically multiarticular, that is that it affects many joints. Once triggered, it results in inflammation of the synovium, leading to edema, vasodilation and activation of CD4+ T cells. Early and intermediate markers of disease progression include the expression of the cytokines; tumour necrosis factor alpha, IL-1, IL-6, IL-8 and IL-15 as well as transforming growth factor (TGF). Once inflammation of the joint occurs, the synovium thickens, while the cartridge disintegrates. This series of events results in joint destruction and loss of joint mobility.

Therapeutic approaches used to treat RA generally target the mediators of inflammation. In particular, tumour necrosis factor inhibitors have been widely prescribed to subject presenting with this condition. Other therapies relate to anti-CD20 antibodies, interleukin-1 (IL-1) blockers, as well as blockers of T cell activation.

Toll-like receptors (TLRs) form a family of pattern recognition receptors which have a key role in activating the innate immune response. 11 Toll-like receptors have been identified in humans to date. The members of the TLR family are highly conserved, with most mammalian species having between 10 to 15 TLRs. Each TLR recognises specific pathogen-associated molecular signatures. Toll-like receptor 2 (TLR2, CD282, TLR-2) is activated by peptidoglycan, lipoproteins and lipoteichoic acid. Toll-like receptors are known to form either homodimers or heterodimers wherein each dimer has a different ligand specificity. TLR2 forms a heterodimer with either TLR1 or TLR6 and perhaps also with TLR10 as a membrane bound receptor. In addition, the ectodomain of TLR2 forms a soluble heterodimers with CD14 in the circulatory system and milk.

Ligand binding to TLR2 results in downstream signalling mediated by interaction with cytoplasmic adaptor proteins such as MyD88 and Mal (MyD88-adaptor like) also known as TIRAP (Toll-Interleukin-1 receptor domain containing adaptor protein). The implication of TLR2 and TLR2-induced signalling and immune system activation has implicated TLR2 as an important mediator in the development of inflammation and disease. Accordingly there has been significant therapeutic interest in relation to the modulation of the TLR2 signalling pathway. It is recognised that the identification that TLR2 mediated immune signaling has importance in inflammation and disease has resulted in a number of therapeutic approaches being designed which serve to block or suppress the function activity of TLR2.

The inventors have surprisingly identified that TLR2-mediated IL-8 (interleukin 8) cytokine production is involved, as an important pro-inflammatory mediator, in the development and progression of rheumatoid arthritis.

Without wishing to be bound by theory, the inventors predict that compounds present in the synovial fluid of subjects presenting with rheumatoid arthritis cause activation of Toll-like Receptor 2 (TLR2), this in turn results in intracellular signalling which is mediated by Toll-like Receptor 2, which causes the expression of mediators, such as pro-inflammatory cytokines, which cause a pro-inflammatory response. In particular, and with reference to the onset and progression of rheumatoid arthritis, the inventors have shown that Toll-like Receptor 2 activation results in intracellular signalling which results in the production of the pro-inflammatory cytokine IL-8, and the associated development of a pro-inflammatory immune response.

The inventors have therefore identified that blocking the activation or suppressing the function or intracellular capability of Toll-like Receptor 2 will, in turn, result in a reduction in the production of IL-8, this in turn causing a down-regulation of the aberrant immune response which characterises the development of rheumatoid arthritis in a subject.

SUMMARY OF THE INVENTION

According to a first aspect of the invention there is provided a method for the treatment and/or prophylaxis of autoimmune arthritis, the method comprising the steps of:
  providing a therapeutically effective amount of an agent which modulates the function of Toll-like Receptor 2, and
  administering said compound to a subject in need of such treatment.

As herein defined, the term 'modulates the function' means that the agent modulates one or more of the biological functional activities of Toll-like Receptor 2. In certain embodiments, the modulation of Toll-like Receptor 2 function relates to an inhibition of the activation of Toll-like Receptor 2 and/or of the inhibition or suppression of downstream intracellular signalling mediated by Toll-like Receptor 2. Modulation may further extend to a suppression of the expression of Toll-like Receptor 2.

As herein defined, an 'agent' which modulates TLR2 is compound which suppresses or blocks the activation or function of Toll-like Receptor 2. The 'agent' may be an antagonist compound which inhibits or blocks the binding of a ligand or binding compound to Toll-like Receptor 2. For example, the 'agent' may be a Toll-like Receptor binding agent which binds to the extracellular domain of Toll-like Receptor 2, said agent inhibiting the binding of TLR2 specific activating ligands. Further, the 'agent' may be a compound which inhibits or suppresses intracellular signalling mediated by Toll-like Receptor 2 following ligand binding and/or Toll-like Receptor 2 activation. The 'agent' may further modulate Toll-like Receptor 2 expression.

In certain embodiments, the 'agent' may be a binding compound which has binding specificity for Toll-like Receptor 2. In certain embodiments, the binding compound is selected from the group comprising of, but not limited to: proteins, peptides, peptidomimetics, nucleic acids, polynucleotides, polysaccharides, oligopeptides, carbohydrates, lipids, small molecule compounds, and naturally occurring compounds, such as plant derived compounds.

In certain embodiments, the agent is a binding compound which binds to Toll-like Receptor 2 at a site other than the ligand binding site, and which, upon binding, causes a change in the confirmation of Toll-like Receptor 2, which leads to an inhibition of Toll-like Receptor 2 agonist binding.

According to one embodiment, TLR2 modulators, including TLR2 binding agents, such as TLR2 antagonists, bind to TLR2 with high affinity, for example, with an affinity constant of at least about $10^7$ $M^{-1}$, typically about $10^8$ $M^{-1}$, and more typically, about $10^9$ $M^{-1}$ to $10^{10}$ $M^{-1}$ or stronger; and modulate, e.g., reduce and/or inhibit, one or more TLR2 biological activities in a TLR2 responsive cell and/or tissue.

In certain embodiments, TLR2 modulator is targeted to Toll-like Receptor 2 expressed on the cells or tissues which comprise the synovial membrane or connective tissue which is localised about a joint region of a subject. The inflamed synovial membrane causes associated joint damage and degradation of the cartilage and bone. Exemplary TLR2 activities that can be modulated, e.g., inhibited or reduced, using the methods and compositions of the invention include, but are not limited to, one or more of the following: (i) inhibiting or suppressing TLR2 expression, (ii) inhibiting TLR2 ligand binding, and (iii) inhibiting or suppressing intracellular signalling mediated by TLR2.

Accordingly, in a further aspect, the invention provides a method of modulating a function (e.g., modulating one or more biological activities of TLR2) in a TLR2— responsive cell and/or tissue (e.g., the cells of the synovial membrane, such as the intima or subintima). The method includes contacting the TLR2-responsive cell and/or TLR2-responsive tissue with a TLR2 modulator, e.g., a TLR2-binding agent, (e.g., an antagonist of human TLR2 activity or expression), in an amount sufficient to modulate the function of the TLR2-responsive cell or tissue (or the biological activity of TLR2 in the cell or tissue). In one embodiment, the contacting step can be effected in vitro, e.g., in a cell lysate or in a reconstituted system. Alternatively, the subject method can be performed on cells in culture, e.g., in vitro or ex vivo. For example, cells (e.g., purified or recombinant cells) can be cultured in vitro and the contacting step can be effected by adding the TLR2 modulator to the culture medium. Typically, the TLR2-responsive cell is a mammalian cell, e.g., a human cell. In some embodiments, the TLR2-responsive cell is a cell of the synovium, for example a cell of the intima or subintima, or cellular population associated therewith. In other embodiments, the method can be performed on cells present in a subject, e.g., as part of an in vivo protocol, or in an animal subject (including, e.g., a human subject, or an in vivo animal model. The in vivo protocol can be therapeutic or prophylactic, and the inflammatory model can be, for example, an EAE model, or a genetically modified model (e.g., an animal model having overexpressed TLR2, or a mutation or deletion in a TLR receptor). For in vivo methods, the TLR2 modulator, alone or in combination with another agent, can be administered to a subject suffering from an autoimmune disease such as rheumatoid arthritis, in an amount sufficient to modulate, one or more TLR2 mediated activities or functions in the subject. In some embodiments, the amount or dosage of the TLR2 modulator that is administered can be determined prior to administration by testing in vitro or ex vivo, the amount of TLR2 modulator required to alter, e.g., decrease or inhibit, one or more of TLR2 activities (e.g., one or more TLR2 biological activities described herein). Optionally, the in vivo method can include the step(s) of identifying (e.g., evaluating, diagnosing, screening, and/or selecting) a subject having, or at risk of having, one or more symptoms associated with the autoimmune disorder or condition.

In certain embodiments where inhibition, reduction or diminution of one or more TLR2 biological activities is desired, the TLR2-responsive cell and/or tissue is contacted with a TLR2 antagonist, e.g., by administering the TLR2 antagonist to the subject. In one embodiment, the TLR2 antagonist interacts with, e.g., binds to, a TLR2 polypeptide or mRNA, and reduces or inhibits one or more TLR2 activities. Typically, the TLR2 antagonized is a mammalian TLR2 (or a functional variant thereof), e.g., human TLR2 or murine TLR2. In certain embodiments, the TLR2 antagonized includes the human TLR2 sequence as defined in FIG. 4 (SEQ ID NO:1) (comprising the 784 amino acid full length human Toll-like Receptor sequence as defined as Genbank Accession Number AAC 34133 (URL www.ncbi.nlm.nih.gov)) or of the murine TLR2 sequence comprising the amino acid sequence defined in FIG. 5 (SEQ ID NO:2) (Genbank Accession Number NP_036035 (*Mus musculus*)), or a portion thereof, and/or a sequence substantially homologous thereto, or encoded by a nucleotide sequence and/or a sequence substantially homologous thereto which encodes the amino acid sequence of SEQ ID NO:1 or SEQ ID NO:2.

In certain embodiments the autoimmune arthritis may be one or more of the group comprising, but not limited to: rheumatoid arthritis, inflammatory arthritis, juvenile rheumatoid arthritis, osteoarthritis and psoriatic arthritis. In further embodiments, the autoimmune arthritis may be collagen-induced arthritis. In further embodiments the autoimmune arthritis may include other inflammatory conditions associated with arthritis.

As herein defined, Toll-like Receptor 2 may be also referred to as TLR2, TLR-2 or CD282. Typically, the Toll-like Receptor 2 is human Toll-like Receptor 2. The amino acid sequence of Toll-like Receptor 2 as derived from humans is defined in Genbank Accession Number AAC 34133, said sequence comprising 784 amino acids. Alternatively, the Toll-like Receptor 2 is murine Toll-like Receptor 2. In further embodiments, the Toll-like receptor 2 is derived from any mammal other than a human or mouse, for example, a cow or rat. In certain further embodiments, the antibody of this aspect of the invention is cross-reactive, that is that it has binding specificity to Toll-like Receptor 2 derived from different species.

The term binding compound means a specific binding agent and refers to a natural or non-natural molecule that specifically binds to a target, in particular an epitope present on TLR2. Examples of suitable binding compounds for use in the present invention include, but are not limited to, proteins, peptides, peptidomimetics, nucleic acids, carbohydrates, lipids, and small molecule compounds.

The term "specifically binds" or "binding specificity" refers to the ability of the binding compound to bind to a target epitope present on TLR2 with a greater affinity than it binds to a non-target epitope. In certain embodiments, specific binding refers to binding to a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method.

In certain embodiments, the binding compound binds to at least one epitope present on TLR2, wherein binding to this epitope results in an inhibition of TLR2 function. An "epitope" refers to a portion of TLR2 which is capable of being recognised by and bound by a binding compound such as a small molecule or antibody by the binding region of said small molecule or antibody. Epitopes generally consist of chemically active surface groups and have specific three dimensional structural characteristics as well as specific charge characteristics. Typically, the binding compound antagonises the binding activity of TLR2 and as such binds to an epitope known as an inhibiting or inhibitory epitope. An "inhibiting" or "inhibitory" epitope means an epitope, that when bound by a binding compound, such as a small molecule or an antibody, results in the loss of biological activity of TLR2. The epitope which is present on TLR2, and which is bound by the binding compounds in order to antagonise TLR2 function, may comprise 5 or more amino acid residues. In certain embodiments, the binding compounds recognise an epitope comprised of at least 5 continuous amino acid residues which is present from amino acid residues 292 to 586 of the amino acid sequence of the extracellular domain of human TLR2 as defined herein in SEQ ID NO:3.

In certain embodiments the binding compound is an antibody, typically a monoclonal antibody. In certain embodiments, the monoclonal antibody may be a murine antibody, a humanised antibody or a camelid antibody. In certain embodiments, the antibody can be of an isotype selected from the group comprising; IgG, IgA, IgM, IgE. In particular, the antibody is of the isotype IgG and may be of the subclass IgG1, IgG2, IgG3 or IgG4.

In functioning to suppress TLR2 activity, typically the TLR2 binding compound reduces, inhibits or antagonises Toll-like receptor 2 function, and in particular Toll-like receptor 2 activation and downstream mediated signalling. The reduction, inhibition or antagonism of Toll-like receptor 2 activity may occur regardless of whether Toll-like receptor 2 forms a heterodimer with Toll-like Receptor 1 or Toll-like Receptor 6. By the term "Toll-like receptor 2 activation and downstream mediated signaling" it is meant any intracellular signaling pathway which is induced by activated TLR2. The signaling pathway may be a TLR-2 specific pathway, or may be a "shared" pathway, wherein the pathway may be activated by other sources, for example, pathways which contribute to the activation of the transcription factor NF-kappaB.

TLR2 is known to dimerise into 2 functional heterodimers. As such, TLR2 can dimerise with TLR1 or TLR6. It is thought that this dimerisation is associated with a discrimination which results in the binding of different microbial constituents. Furthermore, TLR2 may also associate with toll-like Receptor 10.

The inventors have recognised that, in order to provide a therapeutic approach which is comprehensive in suppressing TLR2-mediated inflammation in the joints of subjects presenting with arthritis, it would be desirable to provide a binding compound which has binding specificity for TLR2 regardless of whether a heterodimer is formed with TLR1 or TLR6. In this regard, following extensive experimentation, the inventors have identified an epitope, which, when bound, suppresses TLR2 activity.

In certain embodiments of the invention, where the binding compound is an antibody, the antibody binds to an epitope which comprises residues derived from both the N-terminal and C-terminal portions of the mature extracellular domain of Toll-like receptor 2 (TLR2). In certain embodiments, the epitope may comprise residues 19 to 39 as determined from the 586 amino acid sequence of Toll-like Receptor 2, said amino acids being KEESSNQASLSCDRNGICKGS (SEQ ID NO:4). Further, the binding epitope may further comprise amino acids residues 537 to 549 of Toll-like Receptor 2 as present at the C-terminal region of the amino acid sequence of SEQ ID NO:1, this sequence comprising the amino acids CSCEFLSFTQEQQ (SEQ ID NO:5).

In certain further embodiments, the antibody may have a dissociation constant (Kd) selected from the group consisting of: (i) a dissociation constant between $10^{-7}$M and $10^{-11}$M, (ii) a dissociation constant of between $10^{-8}$M and $10^{-9}$M, (iii) a dissociation constant of between $10^{-9}$M and $10^{-10}$M, (iv) a dissociation constant of between $10^{-11}$M and $10^{-12}$M.

In certain further embodiments, this aspect of the invention further provides for an isolated nucleic acid or vector which encodes the variable domains of the heavy and/or light chains of the immunoglobulin.

In certain further aspects, the present invention provides for the use of a binding compound which has binding specificity for Toll-like Receptor 2, and which functions to suppress the function of Toll-like Receptor 2 in the preparation of a medicament for the treatment of an autoimmune condition or disease, most typically rheumatoid arthritis.

In certain embodiments, the binding compound is an antibody, in particular a monoclonal antibody. In certain embodiments of the invention, where the binding compound is an antibody, the antibody binds to an epitope which comprises residues derived from both the N-terminal and C-terminal portions of the mature extracellular domain of Toll-like receptor 2 (TLR2).

According to a further aspect of the present invention, there is provided a pharmaceutical composition for the treatment of an autoimmune condition or disease, most typically rheumatoid arthritis, the composition comprising a binding compound which has binding specificity for TLR2, along with at least one pharmaceutically acceptable carrier, diluent, solubilizer, emulsifier, preservative and/or adjuvant.

In a specific embodiment, the binding compound is selected from but not limited to the group comprising a polyclonal antibody, a monoclonal, humanized antibody, chimeric antibody or synthesized antibody, fusion protein or fragment thereof, a natural or synthetic chemical compound or a peptidomimetic.

In certain embodiments, the pharmaceutical composition may further comprise a secondary therapeutic agent, such as, but not limited to a cytokine inhibitor, or an immunosuppressant. The immunosuppressant may be at least one of: an anti-CD20 antibody, an anti-TNF antibody, an interleukin-1 (IL-1) blocker, or a blocker of T cell activation.

The inventors have further recognised that the method of treatment for rheumatoid arthritis defined herein, which is based on the use of a binding compound which antagonises the function of TLR2 can be modified to provide a combined medicament, wherein said combined medicament further comprises at least one further compound which serves to suppress the immune response which results in the development of rheumatoid arthritis.

Accordingly, a further aspect of the present invention provides a method for the treatment and/or prophylaxis of rheumatoid arthritis, the method comprising the steps of:

administering a therapeutically effective amount of an agent that inhibits the interaction between Toll-like Receptor 2 and a Toll-like Receptor 2 agonist to a subject in need of treatment, and further administering a therapeutically effective amount of at least one secondary immunosuppressant compound.

In certain embodiments, the secondary immunosuppressant compound may comprise at least one of: an anti-CD20 antibody, an anti-TNF antibody, an interleukin-1 (IL-1) blocker, or a blocker of T cell activation.

In certain embodiments, the secondary compound is selected from the group comprising: a nonsteroidal antiinflammatory agent, an organic gold derivative, D-penicillamine, a 4-aminoquinoline, azathioprine, methotrexate, cyclosporin, an angiogenesis inhibitor, a monoclonal antibody to T cells, a monoclonal antibody to an adhesion molecule, and a monoclonal antibody to a cytokine or growth factor.

In certain embodiments the method comprises the administration of an anti-TLR2 antibody administered simultaneously with an anti-TNF antibody. In certain further embodiments, there is provided an anti-TLR2 antibody administered sequentially with an anti-TNF antibody.

In certain further embodiments, the secondary immunosuppressant compound is a binding compound such as an antibody, antibody fragment, small molecule or peptidomimetic which has binding specificity for, and which inhibits the functional activity of tumour necrosis factor (TNF).

Tumour necrosis factor (TNF-α) is acknowledged as being a key inflammatory mediator responsible for the development of rheumatoid arthritis.

In certain embodiments of the invention where the TLR2 binding compound is an antibody, the invention may provide a bi-specific antibody, that is an antibody which has binding specificity for 2 different targets, wherein said bi-specific antibody has binding specificity for at least one epitope present on the TLR2 receptor which results in the inhibition of the function of TLR2 and binding specificity for at least one of: tumour necrosis factor, CD20, at least one cytokine selected from the group consisting of: IL-1, IL-6, IL-8 and IL-15.

A further aspect of the invention provides for a pharmaceutical composition comprising a therapeutically effective amount of an anti-TLR2 antibody in combination with at least one of: an anti-TNF-alpha antibody, and anti-CD20 antibody, an anti-IL-1 antibody, an anti-IL-6 antibody, an anti-IL-8 antibody, and an anti-IL-15 antibody together with a pharmaceutically effective diluent or carrier.

A further aspect of the present invention provides for the use of a binding compound which antagonises the function of Toll-like Receptor 2 together with a secondary binding compound which binds to, and suppresses the function of at least one inflammatory mediator which mediates the aberrant immune response which is causative of rheumatoid arthritis, in the preparation of a medicament for the treatment of rheumatoid arthritis.

In certain embodiments, the secondary binding compound comprises at least one of: an anti-CD20 antibody, an anti-TNF antibody, an interleukin-1 (IL-1) blocker, or a blocker of T cell activation.

The inventors have further identified the utility of soluble forms of the TLR2 receptor in methods for suppressing the aberrant immune response which is characteristic of the subjects presenting with rheumatoid arthritis wherein the immune system targets self-antigens, most particularly, the cellular structure and components of joints.

As such, in certain further aspects, the invention extends to the provision of soluble forms of Toll-like Receptor 2, said soluble forms being characterised in that they serve to compete with membrane bound TLR2 for ligands which bind and activate TLR2. The binding of TLR2 specific ligands to soluble forms of TLR2 results in a downregulation of TLR2 activation as there is a reduced amount of TLR2 specific ligand available to activate membrane bound TLR2.

Accordingly, a further aspect of the present invention provides a method for the treatment and/or prophylaxis of autoimmune arthritis, the method comprising the steps of:

providing a therapeutically effective amount of a soluble form of Toll-like Receptor 2 or a soluble fragment thereof, and administering the same to a subject in need of such treatment.

In certain embodiments the soluble form of TLR2 is prepared by a recombinant technique. A soluble form of Toll-like Receptor 2 typically comprises the extracellular domain of TLR2 only, and hence the intracellular and transmembrane domains of Toll-like Receptor 2 as defined in Genbank Accession Number AAC 34133 are absent. In certain embodiments, the soluble form of Toll-like Receptor 2 may comprise amino acids 1 to 587 of the defined human Toll-like Receptor 2 sequence. The soluble Toll-like Receptor 2 sequence may be modified by means of the addition, deletion or substitution of 1 or more amino acid residues.

In certain embodiments autoimmune arthritis relates to rheumatoid arthritis. In further embodiments, autoimmune arthritis is collagen-induced arthritis.

In certain embodiments, the soluble form of the Toll-like Receptor 2 is derived from the extracellular domain of TLR2 as defined herein in SEQ ID NO:3. In further embodiments, the soluble form of the soluble Toll-like Receptor 2 is provided from a truncated form of the full length Toll-like Receptor 2 amino acid sequence. Typically, said soluble TLR2 has at least a portion of the amino acid residues comprising the intracellular and/or transmembrane domains deleted or substituted, with these deletions and/or substitutions resulting in the Toll-like Receptor 2 protein being soluble. In certain further embodiments, in addition to a deletion and/or substitution of the intracellular and/or transmembrane domains, a deletion and/or substitution may further be made to the amino acid residues of the extracellular domain. Any such deletion and/or substitution of the amino acid residues of the extracellular domain of the TLR2 may be made so long as the modified version of TLR2 which results is soluble and maintains the binding characteristic of TLR2.

The amino acid sequence of the extracellular domain (ectodomain) of human Toll-like Receptor 2 is provided herein as SEQ ID NO:3. The extracellular domain of the human form of Toll-like Receptor 2 comprises 587 amino acid resides, specifically amino acids 1-587 of the defined 784 amino acid full length human Toll-like Receptor sequence as defined as Genbank Accession Number AAC 34133 (URL www.ncbi.nlm.nih.gov). As herein defined, the ectodomain of TLR2 is the portion of the membrane bound form of TLR2 which extends into the extracellular space.

SEQ ID NO: 3:
mphtlwmvwvlgviislskeessnqaslscdrngickgssgslnsipsgl teavkldlsnnrityisnsdlqrcvnlqalvltsngintieedsfsslgs slehldlsynylsnlssswfkplssltflnllgnpyktlgetslfshltk

```
-continued
lqilrvgnmdtftkiqrkdfagltfleeleidasdlqsyepkslksiqnv shlilhmkqhillleifvdvtssveclelrdtdldtfhfselstgetnsl ikkftfrnvkitdeslfqvmkllnqisgllelefddctlngvgnfrasdn drvidpgkvetltirrlhiprfylfydlstlyslterkritvenskvfl vpcllsqhlksleyldlsenlmveeylknsacedawpslqtlilrqnhla slektgetlltlknltnidisknsfhsmpetcqwpekmkylnlsstrihs vtgcipktleildvsnnnlnlfslnlpqlkelyisrnklmtlpdasllpm llvlkisrnaittfskeqldsfhtlktleaggnnficsceflsftqeqqa lakvlidwpanylcdspshvrgqqvqdvrlsvsech
```

In certain embodiments, the soluble Toll-like Receptor 2 (sTLR2) molecule may be targeted to the synovial fluid in order to enhance the effectiveness of such a therapeutic approach. The targeting of sTLR2 in this way is advantageous as systemic administration of sTLR2 may result in global immunosuppression of the TLR2 ligand.

Targeting of soluble forms of sTLR2 may be provided through the formation of a fusion protein, wherein said fusion protein is comprised of a soluble portion of the TLR2 receptor, typically the extracellular domain or a portion thereof, conjoined to a secondary peptide, typically the Fc receptor binding protein is derived from the heavy chain of an immunoglobulin, typically a human immunoglobulin. The Fc domain has been extensively used to prolong the circulatory half-life of therapeutic proteins.

In a further aspect of the present invention there is provided a method for the treatment or prevention of an immune-cell associated disorder, the method comprising:
  providing a compound which inhibits the expression or function of Toll-like Receptor 2, and
  administering the same to a subject in need to such treatment in an amount sufficient to inhibit or reduce immune cell activity in the subject, therefore preventing the disorder.

In certain embodiments, the immune-cell associated disorder is selected from the group comprising, but not limited to: arthritis, rheumatoid arthritis or juvenile rheumatoid arthritis.

In certain further embodiments, the immune cell associated disorder is at least one member of the group selected from, but not limited to: multiple sclerosis, systemic lupus erthyematosis, psoriatic arthritis, ankylosing spondylitis inflammatory bowel disease and Crohn's disease.

In certain embodiments, the method further comprises administering a secondary therapeutic agent, selected from at least one of the group comprising: a cytokine inhibitor, a growth factor inhibitor, an immunosuppressant, an anti-inflammatory agent, a metabolic agent, an enzyme inhibitor, a cytostatic agent and cytotoxic agent.

In certain further embodiments, the secondary therapeutic compound is selected from the group comprising, but not limited to: a TNF antagonist, for example a soluble forms of the TNF receptor, or an antibody to TNF, an anti-CD20 antibody, and IL-12 antagonist, and IL-15 antagonist, an IL-17 antagonist, an IL-18 antagonist, a pro-inflammatory T cell suppressor, a regulatory T cell promoter, a small molecule, for example methotrexate, leflunomide, rapamycin or an analogue, prodrug or salt thereof, a Cox-2 inhibitor, an NSAID or a p38 inhibitor.

The inventors have identified that TLR2-mediated IL-8 production results following the exposure of TLR2 to synovial fluid isolated from subjects presenting with rheumatoid arthritis. IL-8 functions as a pro-inflammatory cytokine which upregulates the aberrant immune response which is seen to attach the synovium and cause joint deterioration. The inventors have further recognised the utility of downregulating TLR2 activation and signalling by inhibiting the production of the TLR2 protein. Inhibiting the production of TLR2 results in a downregulation of membrane bound TLR2, with this in turn reducing TLR2 signalling. Accordingly, the inventors have further recognised the utility of a therapeutic approach wherein inhibitory nucleic acids are administered in order to inhibit TLR2 protein expression.

Accordingly, a further aspect of the present invention provides a method of suppressing TLR2-mediated IL-8 production, the method comprising the step of:
  providing a therapeutically effective amount of an inhibitory nucleic acid, which blocks the expression of the Toll-like Receptor 2 protein, and
  administering the same to a subject in need of such treatment.

In certain embodiments, the inhibiting nucleic acid may include, but is not limited to; anti-sense oligonucleotides, triple helix molecules, anti-sense DNA, anti-sense RNA, ribozyme, iRNA, miRNA, sRNA, shRNA.

As herein defined, the terms "blocks" and "blocking" when used in relation to gene expression means silencing the expression of a gene. Gene silencing is the switching off of the expression of a gene by a mechanism other than genetic modification. Gene silencing can be mediated at the transcriptional or post-transcriptional level. Transcriptional gene silencing can results in a gene being inaccessible to transcriptional machinery, and can be mediated, for example, by means of histone modifications. Post-transcriptional gene silencing results from the mRNA of a gene being destroyed, this preventing an active gene product, such as a protein, in the present case the TLR2 protein.

Accordingly, in one embodiment this aspect of the present invention provides for the provision of an effective amount of an RNAi (RNA interference) agent, such as an interfering ribonucleic acid (for example an siRNA or shRNA) or a transcription template thereof, such as a DNA encoding an shRNA to a cell type expressed in the joint, for example the cells of the cartilage or the synovium, for use in blocking the expression of the TLR2 protein.

In further embodiments, the inhibitory molecule may be antisense RNA. Antisense causes suppression of gene expression and involves single stranded RNA fragments which physically bind to mRNA, this blocking mRNA translation. Techniques for the preparation of appropriate nucleic acid for use as inhibiting nucleic acids are well known to the person skilled in the art.

According to a further aspect of the invention there is provided the use of an inhibitory nucleic acid which blocks the expression of the Toll-like Receptor 2 protein in the preparation of a medicament for the treatment or rheumatoid arthritis.

In certain embodiments the inhibitory nucleic acid is selected from the group consisting of: anti-sense oligonucleotides, triple helix molecules, anti-sense DNA, anti-sense RNA, ribozyme, iRNA, miRNA, siRNA, shRNA.

According to a yet further aspect of the present invention there is provided a pharmaceutical composition for use in the treatment of rheumatoid arthritis, the composition comprising a therapeutically effective amount of an inhibitory nucleic acid along with at least one of a pharmaceutical carrier or diluent.

In certain embodiments the inhibitory nucleic acid is selected from the group comprising, but not limited to: antisense oligonucleotides, triple helix molecules, anti-sense DNA, anti-sense RNA, ribozyme, iRNA, miRNA, sRNA, shRNA.

In certain embodiments the pharmaceutical composition may further comprise at least one immunosuppressant.

A yet further aspect of the invention provides a TLR2 modulator agent as described hereinbefore for use in the treatment of rheumatoid arthritis.

A still further aspect of the invention provides for the use of a TLR2 modulator agent as defined hereinbefore for use in the preparation of a medicament for the treatment of rheumatoid arthritis.

In a further aspect, the invention extends to the provision of at least one aptamer with binding specificity to Toll-like Receptor 2, which causes blocking or suppression of the functional activity of Toll-like Receptor 2. Techniques for the selection of suitable aptamers will be well known to the person skilled in the art, for example, using SELEX technology.

Accordingly, in various further embodiments, the present invention extends to a method of identifying and isolating nucleic acid ligands which have binding specificity for Toll-like Receptor 2, the method comprising the steps of:
(a) providing a candidate mixture of nucleic acids
(b) contacting a cell expressing Toll-like Receptor 2 with the candidate nucleic acid mixture
(c) selecting nucleic acids which have an increased affinity to Toll-like Receptor 2 relative to the other candidate nucleic acids,
(d) amplifying the selected nucleic acids in order to provide at least one nucleic acid with affinity for Toll-like Receptor 2, and
(e) selecting at least one nucleic acid therefrom which has a high affinity and specificity for Toll-like Receptor 2.

In a yet further aspect of the invention there is provided a method for determining whether an agent inhibits Toll-like Receptor 2 mediated interleukin 8 production, the method comprising the steps of:
(i) contacting a cell expressing Toll-like Receptor 2 with said agent and a Toll-like Receptor 2 agonist, and
(ii) determining the binding of the agent to Toll-like Receptor 2, wherein an increase in the presence of interleukin 8 indicates that the agent does not inhibit Toll-like Receptor 2 mediated interleukin 8 production.

BRIEF DESCRIPTION OF THE FIGURES

The present invention will now be described with reference to the following examples which are provided for the purpose of illustration and are not intended to be construed as being limiting on the present invention wherein:

FIG. 1 graphs (a), (b), (c) and (d) show IL-8 responses from 293 HEK-TLR2 cells stimulated with synovial fluid samples, wherein in graphs (a), (c) and (d), each group of 3 black coloured bars, the leftmost bar represents the results for 0.1% synovial fluid v/v, the centre bar shows the results for 1.0% synovial fluid v/v, while the rightmost bar shows the results for 10% synovial fluid v/v, and wherein graphs (a) and (b) show the results after 6 hours, while graphs (c) and (d) show the results after 24 hours, FIG. 2 graphs (a), (b), (c) and (d) show IL-8 responses from 293 HEK-TLR4 cells stimulated with synovial fluid samples, wherein in each group of 3 black coloured bars, the leftmost bar represents the results for 0.1% synovial fluid v/v, the centre bar shows the results for 1.0% synovial fluid v/v, while the rightmost bar shows the results for 10% synovial fluid v/v, and wherein graphs (a) and (b) show the results after 6 hours, while graphs (c) and (d) show the results after 24 hours, FIG. 3 shows Fold increase in IL-8 from synovial fluid samples over normal synovial fluid in HEK-TLR-2 cells stimulated for 24 hours, wherein in each group of 3 black coloured bars, the leftmost bar represents the results for 0.1% synovial fluid v/v, the centre bar shows the results for 1.0% synovial fluid v/v, while the rightmost bar shows the results for 10% synovial fluid v/v, FIG. 4 shows the amino acid sequence of human Toll-like Receptor 2 (SEQ ID NO:1), FIG. 5 shows the amino acid sequence of murine Toll-like Receptor 2 (SEQ ID NO:2), FIG. 6, graphs A, B and C show the results of IL-1 beta expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301.

FIG. 7, graphs A, B and C show the results of IL-6 expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301, FIG. 8, graphs A, B and C show the results of TNF-alpha expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301, FIG. 9, graphs A, B and C show the results of IFN-gamma expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301, FIG. 10 shows graphs A, B, C, D illustrating the results of IL-1 beta cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha, FIG. 11 shows graphs A, B, C, D illustrating the results of IL-6 cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha, FIG. 12 shows graphs A, B, C, D illustrating the results of TNF-alpha cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys. The TNF-alpha positive control was included in this experiment, but excluded from graphs A, B, C and D as the results ranged from 1012-3103 TNF-alpha pg/ml, and FIG. 13 shows graphs A, B, C, D illustrating the results of IFN-gamma cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha.

DETAILED DESCRIPTION OF THE INVENTION

Figure 14:
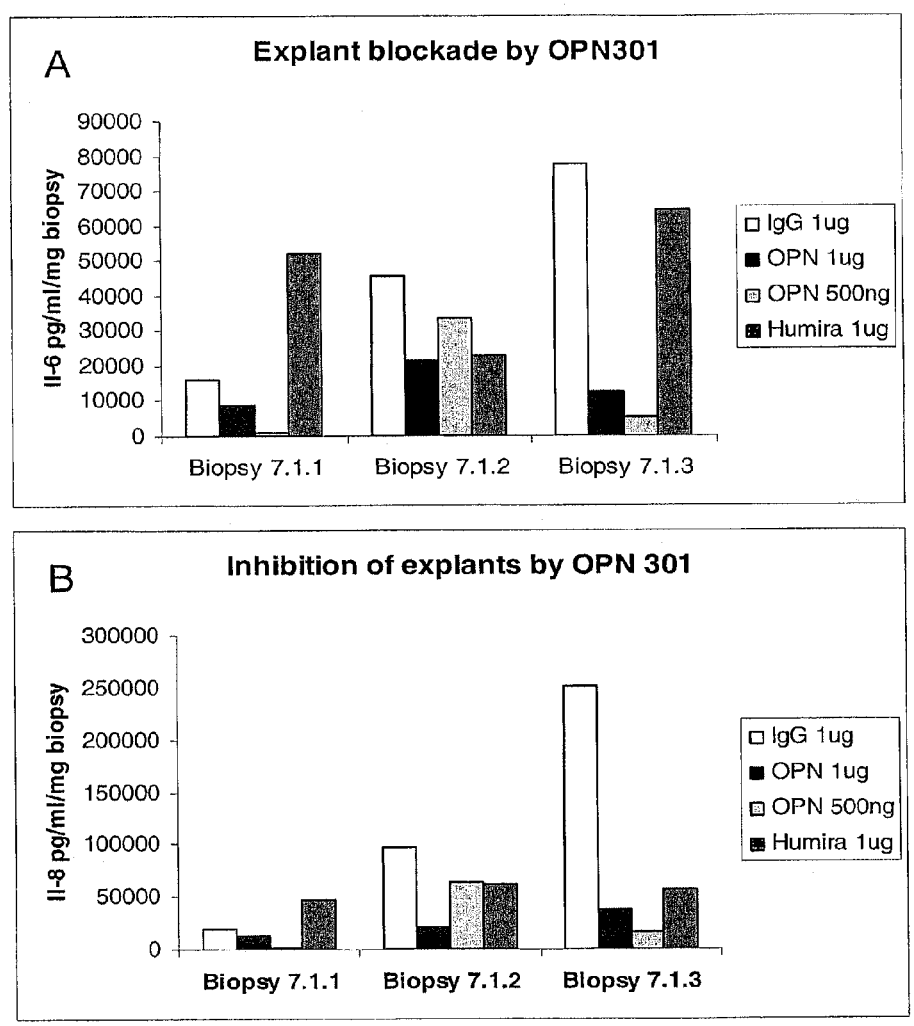
FIG. 14 shows explant inhibition from biopsy samples derived from patient 7, wherein a readout of IL-6 (graph A) or IL-8 (graph B) is shown. In particular, inhibition by the monoclonal antibody OPN-301 given at a dosage of 1 ug and 500 ug. A comparison against an IgG isotype control antibody is shown, as well as a comparison with the commercially available antibody HUMIRA (adalimumab) (Abbott Laboratories Limited), a monoclonal antibody which neutralizes TNF-alpha and which therefore is sued as a TNF inhibitor in the treatment of rheumatoid arthritis is also shown.

The present invention is based, at least in part, a method of reducing one or more biological activities of Toll like receptor 2 (TLR2) in a TLR2 expressing cell or tissue implicated in the onset or progression of autoimmune arthritis, comprising contacting the cell or tissue with an antagonist of TLR2 activity or expression, in an amount sufficient to reduce one or more biological activities of TLR2 in the cell or tissue. In certain embodiments, the TLR2 expressing cell or tissue is a cell of the synovial tissue. In certain embodiments the contacting step occurs in a cell lysate, a reconstituted system or cells in culture. The contacting step may occur on cells present in a subject, and the subject may be a human patient having, or at risk of having autoimmune arthritis. The TLR2 may be human or murine TLR2. In certain embodiments, the antagonist may bind to the extracellular domain of TLR2.

Accordingly, in certain aspects, the present invention provides to binding compounds or fragments thereof which specifically bind to Toll-like Receptor 2 (TLR2) in order to inhibit Toll-like Receptor 2 function. The invention further provides compositions, uses and methods for the treatment of immune-mediated diseases, more particularly autoimmune conditions such as arthritis, and in particular rheumatoid arthritis wherein TLR2-mediated immune cell activation contributes to disease pathology.

Binding compounds which have affinity and binding specificity to the binding epitope of the present invention have utility in the inhibition of number of autoimmune conditions such as rheumatoid arthritis, which are mediated or induced following signalling through Toll-like receptor 2.

As such, the invention provides compositions and methods for the treatment of immune-mediated conditions and inflammatory conditions or pathogenic conditions of the joints, such as rheumatoid arthritis.

In a further aspect, the invention provides a method of evaluating, diagnosing, and/or monitoring the progression of autoimmune arthritis in a in a test sample. The method includes evaluating the expression or activity of a nucleic acid or polypeptide chosen from TLR2 or a TLR2-associated gene, such that a difference in the level of the nucleic acid or polypeptide relative to a reference sample, such as a sample obtained from a normal healthy subject can be determined prior to treatment of the sample so as to determine the presence or progression of the autoimmune arthritis in the subject from whom the test sample is derived. In certain embodiments, the TLR2-associated nucleic acid or polypeptide is characterized by altered expression in response to TLR2 modultory agents of the invention.

In certain embodiments, an increase in the level of TLR2 or a TLR2-associated gene in the test sample, relative to a reference sample, may indicate a likelihood that TLR2 mediated IL-8 production may contribute to the onset and progression of disease pathology as associated with autoimmune arthritis. In other embodiments, a decrease in the level of a TLR2 or a TLR2-associated gene in the test sample, relative to a reference sample, may indicate that a TLR modulator compound according to the invention is acting to reduce the likelihood of the onset or progression of TLR2 mediated autoimmune arthritis.

In certain embodiments, the evaluating step occurs in vitro or ex vivo. For example, a sample, such as a serum sample, is obtained from the subject. In certain further embodiments, the evaluating step occurs in vivo. For example, by administering to the subject a detectably labeled agent that interacts with the TLR2, or TLR2 associated nucleic acid or polypeptide, such that a signal is generated relative to the level of activity or expression of the nucleic acid or polypeptide.

In yet another aspect, the invention provides a method or an assay for identifying a compound, e.g., a test compound, that modulates TLR2 function. The method or the assay may include: providing or identifying a test agent that interacts with (e.g., binds to,) TLR2 or a TLR2-associated protein. The test compound can be an antibody molecule; a peptide; a soluble TLR2 or a fusion thereof; a variant molecule; a small molecule, e.g., a member of a combinatorial or natural product library; a nucleic acid; an antisense molecule; a ribozyme; an RNAi; a triple helix molecule; or any combination thereof. In certain embodiments, the test compound modulates (e.g., decreases or increases) the activity or expression of a TLR2 polypeptide or nucleic acid. For example, the expression of the TLR2 nucleic acid can be modulated by, e.g., altering mRNA transcription and/or altering mRNA stability.

In certain embodiments, the evaluating step includes contacting one or more of: a TLR2 (e.g., a TLR2 as described herein), or a nucleic acid encoding the TLR2, with the test compound; and evaluating a change in one or more activities of the TLR2 polypeptide or nucleic acid encoding the same, in the presence of the test compound, relative to a predetermined level, e.g., a control sample without the test compound. The contacting step can be effected in vitro (in cultured cells, e.g., intima or subintima cells) or in vivo (e.g., by administering the test compound to a non-human subject, e.g., an animal model having autoimmune arthritis or a mutation in a TLR2 or a gene encoding a TLR2 associated protein). The contacting step(s) and/or the administration of the test compound can be repeated.

In one embodiment, the test compound is identified and evaluated in the same or a different assay. For example, a test compound is identified in an in vitro or cell-free system, and evaluated in an animal model or a cell-based assay. Any order or combination of assays can be used. For example, a high throughput assay can be used in combination with an animal model or tissue culture. In other embodiments, the method, or assay includes providing a step based on proximity-dependent signal generation, e.g., a two-hybrid assay that includes a first fusion protein (e.g., a fusion protein comprising a TLR2 portion) and a second fusion protein (e.g., a fusion protein comprising a TLR2-associated polypeptide), and contacting the two-hybrid assay with a test compound under conditions wherein said two hybrid assay detects a change in the formation and/or stability of the complex, e.g., the formation of the complex initiates transcription activation of a reporter gene.

In yet another aspect, the invention provides a host cell comprising one or more nucleic acids encoding one or more of the TLR2 or TLR2-associated polypeptide constituents of the complex disclosed herein.

The term "epitope" as used herein relates to a portion of a macromolecule which is capable of being bound by a specific binding ligand, in this case, a portion of a polypeptide, in particular Toll-like receptor 2. Epitopes may be defined from contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope" is an epitope which is comprised of a series of amino acid residues which are non-linear in alignment, that is that the residues are spaced or grouped in a non-continuous manner along the length of a polypeptide sequence. A non-continuous epitope can be a discontinuous epitope wherein the amino acid residues are grouped into 2 linear sequences, or alternatively the non-continuous epitope can be a discontinuous scattered epitope wherein the residues which contribute to the epitope are provided in 3 or more groups of linear amino acid sequences arranged along the length of the polypeptide.

Antibodies

The antibodies provided by the present invention may be provided by a number of techniques. For example, a combinatorial screening technique such as a phage display-based biopanning assay may be used to in order to identify amino acid sequences which have binding specificity to the binding epitopes of the invention. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In further embodiments, the antibody is a monoclonal antibody may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975), Chimeric antibodies or CDR-grafted antibodies are further provided within the scope of the present invention. In further embodiments, the antibodies of the invention may be produced by the expression of recombinant DNA in host cell.

In further embodiments, humanized antibodies are also provided. Humanized antibodies may be produced by the method of Winter as described in U.S. Pat. No. 5,585,089.

In further certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain further embodiments, the binding compound is a binding fragment which is derived from an antibody, for example, an antibody binding fragment, such as a Fab, F(ab')2, Fv or a single chain Fv (scFV).

In certain further embodiments, the binding compound comprises a polyclonal antibody, a chimeric antibody, a synthesized or synthetic antibody, a fusion protein or fragment thereof, or a natural or synthetic chemical compound or a peptidomimetic.

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

In further embodiments, the antibody may be a Camelid antibody, in particular a Camelid heavy chain antibody. Further the antibody fragment may be a domain antibody or a nanobody derived from a Camelid heavy chain antibody. In a further embodiment the antibody may be a shark antibody or a shark derived antibody.

In certain embodiments, the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies is described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any subclass such as, but not limited to IgG1, IgG2a, IgG2b, IgG3 and IgG4.

The antibody molecules and/or soluble or fusion proteins described herein can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of a TLR2 specific antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or polypeptide, or of a fragment of a TLR2 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR2 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody such as a TLR2 specific antibody and the constant region of a human antibody. Thus the binding member may comprise a human constant region.

The variable region other than the hypervariable region may also be derived from the variable region of a human antibody and/or may also be derived from a monoclonal antibody such as a TLR2 specific antibody. In such case, the entire variable region may be derived from murine monoclonal antibody a TLR2 specific antibody and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-0,184,187, GB 2,188,638A or EP-A-239,400. A hybridoma or other cell producing an antibody may be subject to genetic mutation or other changes, which may or may not alter the binding specificity of antibodies produced.

In certain embodiments, where the TLR2 inhibitory compound or TLR binding compound is an antibody, the antibody is administered to a subject in a therapeutically effective amount. In certain embodiments, the therapeutically effective amount comprises the antibody in a range chosen from 1 µg/kg to 20 mg/kg, 1 g/kg to 10 mg/kg, 1 µg/kg to 1 mg/kg, 10 µg/kg to 1 mg/kg, 10 µg/kg to 100 pg/kg and 500 pg/kg to 1 mg/kg.

Production of Antibodies

Certain methodologies for producing antibodies which have an affinity and binding specificity for the TLR2 epitope of the present invention are described hereinbefore.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is E. coli. The expression of antibodies and antibody fragments in prokaryotic cells such as E. coli is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference.

Techniques for the preparation of recombinant antibody molecules is described in the above references and also in, for example, EP 0623679; EP 0368684 and EP0436S97, which are incorporated herein by reference.

In preferred embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. Examples of such techniques are described in EP 0,239,400 to Winter. In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain κ or λ.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

Antibody Selection Systems

Immunoglobulins which are able to bind to the epitope of the present invention and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in vitro selection and amplification of specific antibody fragments that bind a target antigen. The nucleotide sequences encoding the VH and VL regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci. USA).

An alternative to the use of phage or other cloned libraries is to use nucleic acid, preferably RNA, derived from the B cells of an animal which has been immunised with the selected target, e.g. the TLR2 epitope of the present invention.

Isolation of V-region and C-region mRNA permits antibody fragments, such as Fab or Fv, to be expressed intracellularly. Briefly, RNA is isolated from the B cells of an immunised animal, for example from the spleen of an immunised mouse, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to the TLR2 binding epitope of the present invention may be used to mediate similar diagnostic, prophylactic and therapeutic effects.

Peptidomimetics are typically structurally similar to a template peptide, but have one or more peptide linkages replaced by an alternative linkage, by methods which are well known in the art. For example, a peptide which has a binding specificity for the TLR2 epitope of the invention may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide of and for use in the present invention may be further modified using at least one of C and/or N-terminal capping, and/or cysteine residue capping.

Suitably, a peptide of and for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

Expression, isolation and purification of polypeptides defining the epitope of the invention and fragments thereof may be accomplished by any suitable technique.

A method for producing polypeptides comprises culturing host cells transformed with a recombinant expression vector encoding a polypeptide under conditions that promote expression of the polypeptide, then recovering the expressed polypeptides from the culture. The skilled man will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (*E. coli*) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells. Appropriate cloning and expression vectors for use with mammalian, prokaryotic, yeast, fungal and insect cellular hosts are described, for example, in Pouwels et al. Cloning Vectors: A Laboratory Manual, Elsevier, New York, (1986) (ISBN 0444904018).

Small Molecules

In various further aspects, the present invention relates to screening and assay methods for use in identifying compounds which antagonise TLR2 activity. Certain further aspects extend to the compounds identified thereby, wherein said binding compounds have affinity and binding specificity for the epitope of the invention.

A substance identified as a ligand of the TLR2 receptor may be a peptide or may be non-peptide in nature, for example a peptidomimetic as described hereinbefore. However, non-peptide "small molecules" are often preferred for many in-vivo pharmaceutical uses. Accordingly, a mimetic or mimic of a TLR2 binding compound for use in the present invention may be designed for pharmaceutical uses.

The designing of mimetics to a known pharmaceutically active compound is a known approach to the development of pharmaceuticals based on a "lead" compound. This might be desirable where the active compound is difficult or expensive to synthesise, or where it is unsuitable for a particular method of administration. For example, peptides are not well suited as active agents for oral compositions and administration as they are degraded by proteases present in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, for example by substituting each amino acid residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the TLR2 binding compound is modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

In certain embodiments, the mimetic binding compound may be a natural or synthetic chemical compound used in drug screening programs. Extracts of plants which contain several characterised or uncharacterised components may also be used.

A candidate binding compound which has affinity and binding specificity to TLR2 may be isolated and/or purified, manufactured and/or used to modulate TLR2 functional activity.

In yet further aspects, the invention extends to the use of combinatorial library technology (Schultz, J S (1996) Biotechnol. Prog. 12:729-743) which provides an efficient way of testing a potentially vast number of different substances for ability their ability to bind to an epitope or to modulate the activity of a ligand which binds to an epitope. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trail and error depending upon the type of compound used. Typically, from about 0.01 to 100 nM concentrations of inhibitor compound may be used, for example from 0.1 to 10 nM. Greater concentrations may be used when a peptide is the test substance.

Combination Medicaments

As described hereinbefore, the present invention extends to combinational therapies wherein compositions or methods relates to the administration of a binding compound which inhibits the functional activity of TLR2 are administered in combination with at least one further therapeutic compound which serves to suppress the immune response which is causative of arthritis.

Typically the primary and secondary therapeutic compositions are given contemporaneously. In certain embodiments, the primary therapeutic composition (i.e. the binding compound which antagonises the functional activity of TLR2) and the secondary therapeutic compounds are administered simultaneously. In certain further embodiments, they are administered sequentially.

In certain embodiments, the combination therapy may comprise a TLR2 functional inhibitor which is co-administered to a subject along with at least one of: a cytokine inhibitor (such as, but not limited to an inhibitor of IL-1, IL-6, IL-8 and IL-15), and inhibitor of tumour necrosis factor, a growth factor inhibitor, an immunosuppressor, an anti-inflammatory, an enzymatic inhibitor, a metabolic inhibitor, a cytotoxic agent or a cytostatic agent.

A person of relevant skill in the field will recognise that the administration to a subject of a combination therapy can be advantageous in that it permits administration of a lower dose of therapeutic to a subject in order to achieve and associated therapeutically effective effect. The administration of a lower combined dose also results in the subject being exposed to a lower toxicity level. Furthermore, as the secondary therapeutic compounds which are administered as part of the combination therapy provided by the invention target different pathways, there is likely to be a synergistic improvement in the overall efficacy of the therapy. An improvement in efficacy would again result in the need for a lower dose to be administered and as such an associated reduction in toxicity.

In identifying and selecting suitable secondary therapeutic compound for administration along with the TLR2 inhibitory compounds of the present invention, said secondary therapeutic compounds may be selected on the basis of such compounds modulating the immune response at a different stage of the auto-immune response which characterises arthritis. Such secondary compounds may include, but are not limited to; soluble receptors, peptide inhibitor compound, small molecule, fusion proteins or ligands, antibodies, and cytokines which mediate an anti-inflammatory effect.

As mentioned above, in certain embodiments, the secondary therapeutic compound may be an compound which inhibits the production of a pro-inflammatory cytokine, or a compound which inhibits the function of a pro-inflammatory cytokine. Examples of pro-inflammatory cytokines which may contribute to the pathogenesis of arthritis include, but are not limited to: IL-1, IL-2, IL-6, IL-7, IL-8, IL-12, IL-15, and IL-18. Furthermore cytokines such as tumour necrosis factor alpha (TNF), and GM-CSF have also been identified a having a role in disease pathology of arthritis and as such, their function may be a target for inhibition by the secondary therapeutic compound.

In certain further embodiments, the secondary therapeutic compound is an inhibitor of a cell surface molecule, such as, but not limited to: CD4, CD8, CD25, CD40, CD45, CD69, CD80, CD86 or further to ligands of these receptors, such as CD40L, ICAM-1 and VCAM-1.

In certain further embodiments, the secondary therapeutic compound is an antibody of binding fragment derived therefrom. In certain the examples, the antibody may have binding specificity for TNF, CD20, IL-12, IL-1 or IL-18 or receptors thereof.

In certain further embodiments, the secondary therapeutic compound may be the anti-human TNF antibody HUMIRA (U.S. Pat. No. 6,258,562) of BASF, the chimeric anti-TNF alpha antibody REMICADE (Centocor), a soluble TNF receptor such as a fusion protein comprising a soluble portion of the TNF receptor along with a portion of the Fc domain of an antibody, for example, the therapeutic Etanercept (EN-BREL™) (Immunex, USA). Also included are enzyme antagonists such as TNFalpha converting enzymes (TACE).

Administration

The monoclonal antibody or fusion protein of the present invention may be administered alone but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol, ethanol and the like.

The monoclonal antibody or fusion protein of the present invention may be administered to a patient in need of treatment via any suitable route. As detailed herein, it is preferred that the composition is administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal.

Routes of administration may further include topical and enteral, for example, mucosal (including pulmonary), oral, nasal, rectal.

In preferred embodiments, the composition is deliverable as an injectable composition. For intravenous, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The compositions of the invention are typically administered to a subject in a "therapeutically effective amount", this being sufficient to show benefit to the individual to whom the composition is administered. Typically, the therapeutically effective amount will be an amount sufficient to suppress, prevent or alleviate at least one symptom of rheumatoid arthritis which may include, but is not limited to; inflammation, swelling, abnormal neovascularisation, bone erosion and cartilage erosion.

The actual dose administered, and rate and time-course of administration, will depend on, and can be determined with due reference to, the nature and severity of the condition which is being treated, as well as factors such as the age, sex and weight of the patient to be treated and the route of administration. Further due consideration should be given to the properties of the composition, for example, its binding activity and in-vivo plasma life, the concentration of the fusion protein in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day.

The TLR2 epitope binding compound of the present invention is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The term "or" is used herein to mean, and is used interchangeably with, the term "and/or", unless context clearly indicates otherwise.

As used herein, the terms "about" and "approximately" shall generally mean an acceptable degree of error for the quantity measured given the nature or precision of the measurements. Exemplary degrees of error are within 20 percent (%), typically within 10%, and more typically, within 5% of a given value or range of values. In the context of a range value for an amino acid or nucleotide sequence, the term "about" includes a range that differs by 1, 2, 3, 4 or 5 residues or nucleotides at one or both end points. For example, the phrase "about amino acids 9 to 22" of a sequence can include amino acid sequences, such as 7 to 23 and 11 to 20 of the amino acid sequence specified.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "therapeutically effective amount" means the amount of a fusion protein of the invention which is required to reduce the severity of and/or ameliorate a TLR2 mediated disease, a cancerous condition or a disease such as an autoimmune disease or a neurodegenerative disease or at least one symptom thereof.

As used herein, the term "prophylactically effective amount" relates to the amount of a composition which is required to prevent the initial onset, progression or recurrence of a TLR2 mediated or induced disease or condition, or a disease such as an autoimmune disease or a neurodegenerative disease or at least one symptom thereof in a subject following the administration of the compounds of the present invention.

As used herein, the term "treatment" and associated terms such as "treat" and "treating" means the reduction of the progression, severity and/or duration of a TLR2 mediated condition of at least one symptom thereof, wherein said reduction or amelioration results from the administration of a binding compound which has specificity for the TLR2 binding epitope of the present invention. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

All publications, patent applications, patents, and other references mentioned herein are incorporated by reference in their entirety.

Other features and advantages of the invention will be apparent from the description, drawings and from the claims.

EXAMPLES

Example 1

The experiments in this example served to determine the response, as measured by IL-8 cytokine production, from HEK-293 cells transfected with TLR-2 and HEK-293 cells transfected with TLR-4 stimulated with normal synovial fluid from Asterand and synovial fluid samples.

Methods

Reagents

1) Toll-like Receptor 2 agonist Pam3CSK4 (Invivogen, catalogue number tlr-pms, lot 28-08-pms).
2) OPN301 anti-TLR2 monoclonal antibody (mouse Toll-like Receptor 2 (TLR2) antibody, clone T2.5, HyCult Biotechnology b.v., Cell Sciences, Canton, USA: catalogue number 1054).
3) HEK 293-hTLR1/2 cells (Invivogen, catalogue number 293-htlr1/2) and HEK-TLR-4 cells.

HEK-TLR-2 or HEK-TLR-4 cells were cultured in triplicate overnight at $1 \times 10^5$/ml at 37° C. in 96 well plates. Serial dilutions (10%, 1% and 0.1% v/v) of synovial fluid were then added and the cells cultured for a further 6 and 24 hours. On each separate 96 well plate, cells were also stimulated with media only as a negative control, or in the case of TLR-2 cells Pam3CSK4 at 100 ng/ml and 100 ng/ml LPS (lipopolysaccharide) for TLR-4 cells. Supernatant was removed and assayed for human IL-8 by a specific human RnD DuoSet ELISA (R&D Systems). The synovial fluid (SF) samples were obtained from patients and shown in Table 1.

TABLE 1

| SF# | Sample Identification |
|---|---|
| 1 | 118121 CW 22.02.91 |
| 2 | PETER 23.08.91 |
| 3 | A. Jackson 14.9.93 |
| 4 | L929 10.3.93 |
| 5 | JMcM 118749 8/2 |
| 6 | 267939 DC 11.1.91 |
| 7 | SIMON 23.8.91 |
| 8 | AR 4.3.91 |
| 9 | STEPHEN 18.2.93 |
| 10 | L929 Joe 5/2 |
| N | Normal Synovial fluid. Asterand lot 20186A9 |

Results

FIGS. 1(a) to (d) show IL-8 responses from 293 HEK-TLR2 cells stimulated with synovial fluid samples. Increased production of IL-8 can be seen from synovial fluid samples which are derived from subjects who present with rheumatoid arthritis. This can most clearly be seen around the 24 hour time point (FIGS. 1(c) and (d)).

FIGS. 2(a) to (d) show IL-8 responses from 293 HEK-TLR4 cells stimulated with synovial fluid samples. High background levels of IL-8 production are seen. There is no apparent difference between IL-8 production induced by synovial fluid derived from subjects presenting with or without RA.

FIG. 3 shows the level of (fold) increase in IL-8 production induced by synovial fluid samples over normal synovial fluid in HEK-TLR-2 cells stimulated for 24 hours. It can be seen that in all cases, synovial fluid samples obtained from subjects presenting with rheumatoid arthritis present induce higher levels of IL-8 production, when compared with the level of IL-8 production induced by synovial fluid obtained from a subject who does not present with rheumatoid arthritis.

Discussion

It is shown that synovial fluid samples cause an increase in IL-8 cytokine production from 293 HEK-TLR-2 cells when compared to normal synovial fluid. This upregulation of IL-8 production is particularity apparent at the 24 hour time point. Approximately a 4 fold increase would be required in order to observe a relevant inhibition by the OPN-301 anti-TLR2 monoclonal antibody. It should be noted that the 4 fold increase is the Minimum Fold increase and is an arbitrary figure chosen such that a statistically and scientifically significant level of inhibition could be observed were the OPN-301 anti-TLR2 monoclonal antibody is added to cultures stimulated with synovial fluid.

In this regard, sample 3 and possibly samples 1, 2, 6, 9, and 10 as detailed in Table 1 meet with this criteria. Although no apparent dose response was observed between the various dilutions of synovial fluid this may simply mean that at 0.1% v/v synovial fluid or lower a saturated level of soluble TLR-2 ligand is present above which no further increase in the level of IL-8 will be observed. High background secretion of IL-8 was observed in 293-HEK-TLR-4 cells and neither normal nor sample synovial fluid was observed to enhance this suggesting there are no TLR-4 ligands present in any of the synovial fluid samples tested. The primary conclusion which can be drawn from these experiments is that these samples contain some soluble TLR-2 ligands.

Example 2

Cytokine Expression Profiles in Synovial Tissue Biopsy Samples Exposed to TLR2 Agonist and Antagonist Explant Experiments:

Tissue biopsies of synovial tissue were removed from a human patient during an arthroscopy procedure. Each biopsy sample was cut into 4 pieces and placed in a well of a 96-well plate containing media. Each well contained a different combination of either a Toll-like Receptor 2 antagonist and/or a Toll-like Receptor 2 agonist.

The Toll-like Receptor 2 antagonist was the anti-TLR2 monoclonal antibody OPN-301 ((OPN301) mouse Toll-like Receptor 2 (TLR2) antibody, clone T2.5, HyCult Biotechnology b.v., Cell Sciences, Canton, USA: catalogue number 1054)). Where the effect of the OPN-301 anti-TLR2 antibody on TLR2 activation and cytokine production in the explant sample was to be assessed, each piece of the 3 biopsy samples were incubated in full media with the anti-TLR2 OPN-301 antibody, or an IgG isotype control antibody (catalogue mab002, clone 1711, mouse IgG1 monoclonal antibody (RnD Systems)) for 72 hours (3 biopsies in total).

Where the effect of the TLR2 antagonist, OPN-301, was to be assessed, the biopsy samples were incubated in full media along with the OPN-301 anti-TLR2 monoclonal antibody which was added at a concentration of either 1 μg or 1 ng. Control samples were set up wherein the addition of the OPN-301 monoclonal antibody was replaced by the addition of an IgG isotype control antibody, as described above.

The wells containing the 4th piece of the biopsy samples had the anti-TNFalpha antibody HUMIRA (adalimumab) added.

The samples (3 synovial tissue biopsy samples) were then incubated for 72 hours.

The expression profile of the cytokines IL-1 beta, IL-6, TNF-alpha and IFN-gamma was determined. The results of these cytokine expression profiles are shown in FIGS. 6 (IL-1 beta), 7 (IL-6), 8 (TNF-alpha) and 9 (IFN-gamma).

In order to determine the cytokine profile produced following TLR2 activation in the absence of a TLR2 antagonist, pieces of the biopsy samples were serum starved for 24 hours and then stimulated with the TLR2 antagonist Pam3Cys for 24 hours. 4 synovial tissue biopsy samples were assessed in total, 2 of these samples being exposed to 200 ng or 1 μg of Pam3Cys, while the further 2 were exposed to 200 ng and 10 μg Pam3Cys.

The resulting cytokine expression profiles are shown in FIGS. 10 (IL-1 beta), 11 (IL-6), 12 (TNF-alpha) and 13 (IFN-gamma).

Results

FIG. 6, graphs A, B and C show the results of IL-1 beta expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301.

FIG. 7, graphs A, B and C show the results of IL-6 expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301.

FIG. 8, graphs A, B and C show the results of TNF-alpha expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301.

FIG. 9, graphs A, B and C show the results of IFN-gamma expression from pieces of 3 separate synovial tissue biopsy samples obtained from a patient. IgG shows the IgG isotype control antibody MAB002, Humira shows the anti-TNFalpha monoclonal antibody HUMIRA (adalimumab), OPN is the anti-TLR2 monoclonal antibody OPN-301.

FIG. 10 shows graphs A, B, C, D illustrating the results of IL-1 beta cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha.

FIG. 11 shows graphs A, B, C, D illustrating the results of IL-6 cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha.

FIG. 12 shows graphs A, B, C, D illustrating the results of TNF-alpha cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys. The TNF-alpha positive control was included in this experiment, but excluded from graphs A, B, C and D as the results ranged from 1012-3103 TNF-alpha pg/ml.

FIG. 13 shows graphs A, B, C, D illustrating the results of IFN-gamma cytokine expression from a piece of 4 separate synovial tissue biopsy samples. Basal illustrates the cytokine expression level without the addition of the TLR2 agonist Pam3Cys. Pam shows the addition of 2 separate concentrations of Pam3Cys, while TNF shows the addition of the cytokine TNF-alpha.

Example 3

IL-6 and IL-8 Cytokine Expression Profiles in Tissue Biopsy Samples Exposed to TLR2 Antagonistic Antibody Biopsies were removed from 3 different patients at arthroscopy. Each biopsy was cut into 4 pieces and placed in a well of a 96-well plate containing media+/−inhibitors/stimulant.

Figure 15:
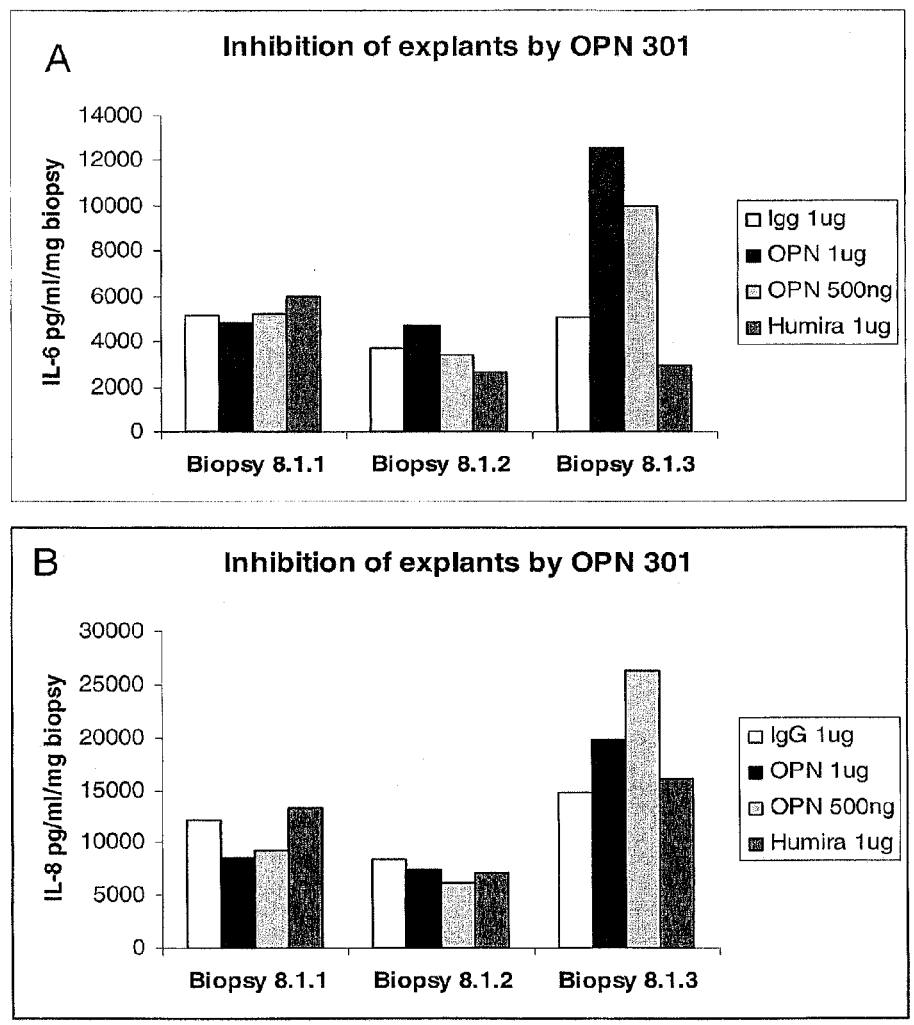
FIG. 15 shows explant inhibition from biopsy samples derived from patient 8, wherein a readout of IL-6 (graph A) or IL-8 (graph B) is shown. In particular, inhibition by the monoclonal antibody OPN-301 given at a dosage of 1 ug and 500 ug. A comparison against an IgG isotype control antibody is shown, as well as a comparison with the commercially available antibody HUMIRA (adalimumab) (Abbott Laboratories Limited), a monoclonal antibody which neutralizes TNF-alpha and which therefore is sued as a TNF inhibitor in the treatment of rheumatoid arthritis is also shown.

For the OPN301 monoclonal antibody blockade experiment (the results of which are shown in FIGS. 14 and 15), biopsies were incubated in full-media+IgG or the OPN 301 monoclonal antibody for 72 hours.

Figure 16:
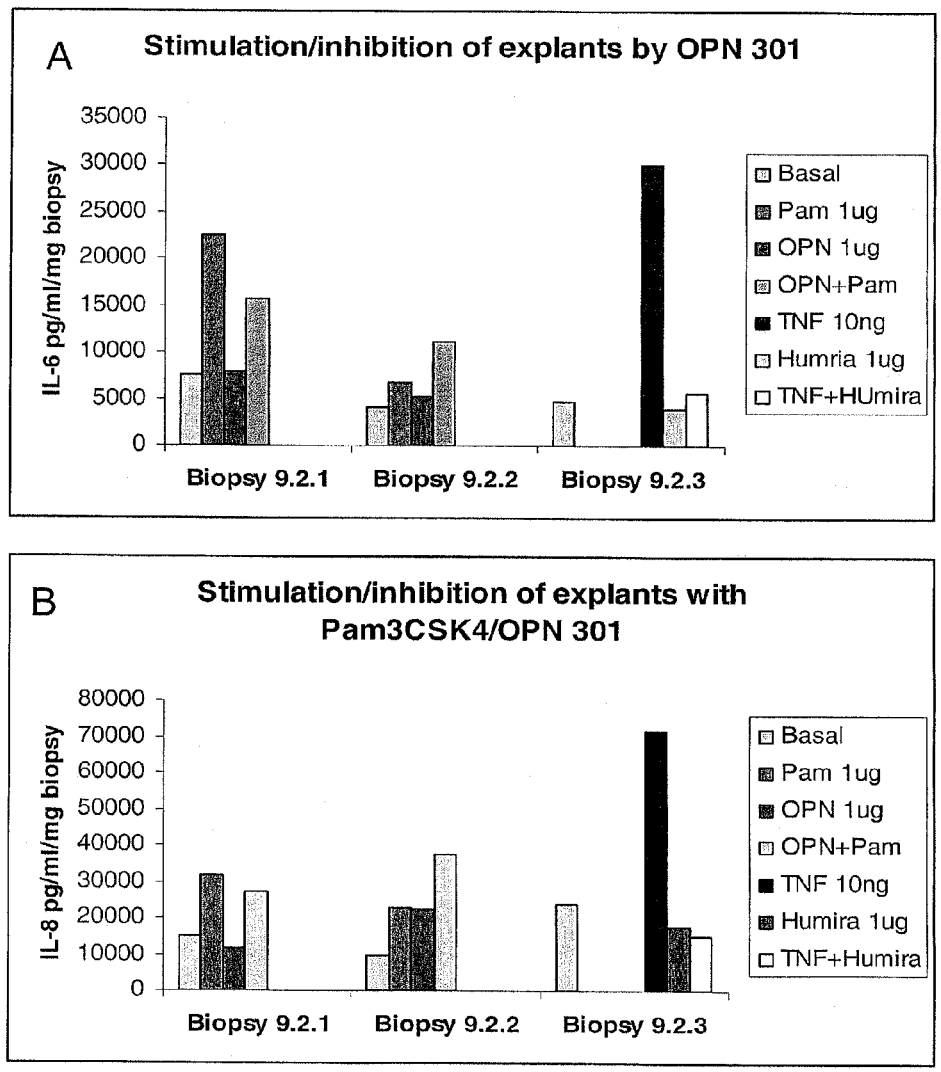
FIG. 16 shows the stimulation and/or inhibition of explants with anti-TLR2 monoclonal antibody OPN301 (graph A) or with the toll-like receptor agonist Pam3CSK4 along with the monoclonal antibody OPN301 (graph B). A comparison against an IgG isotype control antibody is shown, as well as a comparison with the commercially available antibody HUMIRA (adalimumab) (Abbott Laboratories Limited), a monoclonal antibody which neutralizes TNF-alpha and which therefore is sued as a TNF inhibitor in the treatment of rheumatoid arthritis is also shown.

For the stimulation/blockade experiments (the results of which are shown in FIG. 16), biopsies were serum starved for 24 hours and stimulated/inhibited with Pam3Cys/OPN301 for 24 hours.

The results are shown in graphs A (showing IL-6 production) or B (showing IL-8 production) of FIGS. 14, 15 and 16 for samples derived from patient numbered 7, 8 and 9 respectively.

FIG. 14 shows explant inhibition from biopsy samples derived from patient 7, wherein a readout of IL-6 (graph A) or IL-8 (graph B) is shown. In particular, inhibition by the monoclonal antibody OPN-301 given at a dosage of 1 ug and 500 ug.

FIG. 15 shows explant inhibition from biopsy samples derived from patient 8, wherein a readout of IL-6 (graph A) or IL-8 (graph B) is shown. In particular, inhibition by the monoclonal antibody OPN-301 given at a dosage of 1 ug and 500 ug.

FIG. 16 shows the stimulation and/or inhibition of explants with anti-TLR2 monoclonal antibody OPN301 (graph A) or with the toll-like receptor agonist Pam3CSK4 along with the monoclonal antibody OPN301 (graph B).

In each of FIGS. 14, 15 and 16, a comparison against an IgG isotype control antibody is shown, as well as a comparison with the commercially available antibody HUMIRA (adalimumab) (Abbott Laboratories Limited), a monoclonal antibody which neutralizes TNF-alpha and which therefore is sued as a TNF inhibitor in the treatment of rheumatoid arthritis.

Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for the treatment of rheumatoid arthritis, the method comprising the step of:
administering a therapeutically effective amount of a pharmaceutical composition consisting of an antibody or binding fragment thereof which antagonizes the function of Toll-like Receptor 2 to a subject in need of such treatment.

2. The method as claimed in claim 1, wherein the therapeutically effective amount is administered to the subject in order to reduce or inhibit one or more TLR2 biological activities in a TLR2 expressing cell or tissue of the synovium.

3. The method of claim 2, wherein the antibody is a human, camelid, or in vitro generated antibody to human TLR2.

4. The method as claimed in claim 2, wherein the antibody is selected from the group consisting of:
(a) a chimeric antibody or fragment thereof,
(b) a synthetic antibody or fragment thereof,
(c) a humanised antibody or a fragment thereof, and
(d) a Fab fragment.

5. The method as claimed in claim 2, wherein the antibody is of an isotype selected from the group consisting of lgG, IgA, IgM, and IgE.

6. The method as claimed in claim 1, wherein the TLR2 antagonistic antibody binds to the extracellular domain of human TLR2.

7. The method as claimed in claim 1, wherein the antibody is selected from the group consisting of a monoclonal antibody, a polyclonal antibody and a human antibody.

8. The method as claimed in claim 1, wherein the antibody binds to an inhibitory epitope present on Toll-like Receptor 2 with a dissociation constant (Kd) selected from the group of from $10^{-7}$M to $10^{-11}$M.

9. The method as claimed in claim 1, wherein the Toll-like Receptor 2 is human Toll-like Receptor 2 or murine Toll-like Receptor 2.

10. The method of claim 1, wherein the TLR2 antagonistic antibody is the anti-TLR2 monoclonal antibody from the clone T2.5 or a humanised version of the antibody or a fragment thereof which acts as an antagonist of TLR2 activity or expression.

11. A method for the treatment of rheumatoid arthritis, the method comprising the step of:
   administering a therapeutically effective amount of a pharmaceutical composition consisting of an antibody or binding fragment thereof which antagonizes the function of Toll-like Receptor 2 and one or more compounds selected from the group consisting of a pharmaceutically acceptable carrier, a diluent, a solubilizer, an emulsifier, a preservative and an adjuvant to a subject in need of such treatment.

12. A method for the treatment of rheumatoid arthritis, the method consisting of the steps of:
   administering a therapeutically effective amount of an antibody or binding fragment thereof which antagonizes the function of Toll-like Receptor 2 to a subject in need of such treatment; and
   administering to the subject an immunosuppressant compound selected from the group consisting of an anti-CD20 antibody, an anti-TNF antibody, an interleukin-1 blocker, a blocker of T cell activation, a non-steroidal anti-inflammatory agent, an organic gold derivative, D-penicillamine, 4-aminoquinoline, azathioprine, methotrexate, cyclosporine, an angiogenesis inhibitor, a monoclonal antibody with binding specificity to T cells, a monoclonal antibody with binding specificity to an adhesion molecule and a monoclonal antibody with binding specificity to a cytokine or a growth factor.

13. A method for the treatment of rheumatoid arthritis, the method consisting of the steps of:
   administering a therapeutically effective amount of an antibody or binding fragment thereof which antagonizes the function of Toll-like Receptor 2 and one or more compounds selected from the group consisting of a pharmaceutically acceptable carrier, a diluent, a solubilizer, an emulsifier, a preservative and an adjuvant to a subject in need of such treatment; and
   administering to the subject an immunosuppressant compound selected from the group consisting of an anti-CD20 antibody, an anti-TNF antibody, an interleukin-1 blocker, a blocker of T cell activation, a non-steroidal anti-inflammatory agent, an organic gold derivative, D-penicillamine, 4-aminoquinoline, azathioprine, methotrexate, cyclosporine, an angiogenesis inhibitor, a monoclonal antibody with binding specificity to T cells, a monoclonal antibody with binding specificity to an adhesion molecule and a monoclonal antibody with binding specificity to a cytokine or a growth factor.

* * * * *

UNITED STATES PATENT AND TRADEMARK OFFICE
CERTIFICATE OF CORRECTION

PATENT NO.         : 8,580,255 B2                                              Page 1 of 1
APPLICATION NO.    : 12/666442
DATED              : November 12, 2013
INVENTOR(S)        : Mark Heffernan et al.

It is certified that error appears in the above-identified patent and that said Letters Patent is hereby corrected as shown below:

In the Claims:

Column 42, claim 5, line 55, delete "1gG" and insert --IgG--.

Signed and Sealed this
Fifteenth Day of April, 2014

Michelle K. Lee
*Deputy Director of the United States Patent and Trademark Office*

SEQUENCE LISTING

<160> NUMBER OF SEQ ID NOS: 5

<210> SEQ ID NO 1
<211> LENGTH: 784
<212> TYPE: PRT
<213> ORGANISM: Homo sapiens

<400> SEQUENCE: 1

```
Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365
```

```
Glu Asn Leu Met Val Glu Glu Tyr Leu Lys Asn Ser Ala Cys Glu Asp
        370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
                435                 440                 445

His Ser Val Thr Gly Cys Ile Pro Lys Thr Leu Glu Ile Leu Asp Val
        450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
        530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
        610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
        675                 680                 685

Ile Ile Asp Ser Ile Glu Lys Ser His Lys Thr Val Phe Val Leu Ser
        690                 695                 700

Glu Asn Phe Val Lys Ser Glu Trp Cys Lys Tyr Glu Leu Asp Phe Ser
705                 710                 715                 720

His Phe Arg Leu Phe Glu Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
        755                 760                 765

Ala Gln Arg Glu Gly Phe Trp Val Asn Leu Arg Ala Ala Ile Lys Ser
770                 775                 780
```

<210> SEQ ID NO 2
<211> LENGTH: 784
<212> TYPE: PRT
<213> ORGANISM: Mus musculus

<400> SEQUENCE: 2

Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
            20                  25                  30

Ser Gly Val Cys Asp Gly Arg Ser Arg Ser Phe Thr Ser Ile Pro Ser
        35                  40                  45

Gly Leu Thr Ala Ala Met Lys Ser Leu Asp Leu Ser Phe Asn Lys Ile
    50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asp Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
    130                 135                 140

Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
                165                 170                 175

Asn Glu Leu Glu Ile Lys Ala Leu Ser Leu Arg Asn Tyr Gln Ser Gln
            180                 185                 190

Ser Leu Lys Ser Ile Arg Asp Ile His His Leu Thr Leu His Leu Ser
        195                 200                 205

Glu Ser Ala Phe Leu Leu Glu Ile Phe Ala Asp Ile Leu Ser Ser Val
    210                 215                 220

Arg Tyr Leu Glu Leu Arg Asp Thr Asn Leu Ala Arg Phe Gln Phe Ser
225                 230                 235                 240

Pro Leu Pro Val Asp Glu Val Ser Ser Pro Met Lys Lys Leu Ala Phe
                245                 250                 255

Arg Gly Ser Val Leu Thr Asp Glu Ser Phe Asn Glu Leu Leu Lys Leu
            260                 265                 270

Leu Arg Tyr Ile Leu Glu Leu Ser Glu Val Glu Phe Asp Asp Cys Thr
        275                 280                 285

Leu Asn Gly Leu Gly Asp Phe Asn Pro Ser Glu Ser Asp Val Val Ser
    290                 295                 300

Glu Leu Gly Lys Val Glu Thr Val Thr Ile Arg Arg Leu His Ile Pro
305                 310                 315                 320

Gln Phe Tyr Leu Phe Tyr Asp Leu Ser Thr Val Tyr Ser Leu Leu Glu
                325                 330                 335

Lys Val Lys Arg Ile Thr Val Glu Asn Ser Lys Val Phe Leu Val Pro
            340                 345                 350

Cys Ser Phe Ser Gln His Leu Lys Ser Leu Glu Phe Leu Asp Leu Ser
        355                 360                 365

Glu Asn Leu Met Val Glu Glu Tyr Leu Lys Asn Ser Ala Cys Lys Gly
    370                 375                 380

Ala Trp Pro Ser Leu Gln Thr Leu Val Leu Ser Gln Asn His Leu Arg

-continued

```
                385                 390                 395                 400
Ser Met Gln Lys Thr Gly Glu Ile Leu Leu Thr Leu Lys Asn Leu Thr
                    405                 410                 415
Ser Leu Asp Ile Ser Arg Asn Thr Phe His Pro Met Pro Asp Ser Cys
                420                 425                 430
Gln Trp Pro Glu Lys Met Arg Phe Leu Asn Leu Ser Ser Thr Gly Ile
            435                 440                 445
Arg Val Val Lys Thr Cys Ile Pro Gln Thr Leu Glu Val Leu Asp Val
        450                 455                 460
Ser Asn Asn Asn Leu Asp Ser Phe Ser Leu Phe Leu Pro Arg Leu Gln
465                 470                 475                 480
Glu Leu Tyr Ile Ser Arg Asn Lys Leu Lys Thr Leu Pro Asp Ala Ser
                485                 490                 495
Leu Phe Pro Val Leu Leu Val Met Lys Ile Arg Glu Asn Ala Val Ser
                    500                 505                 510
Thr Phe Ser Lys Asp Gln Leu Gly Ser Phe Pro Lys Leu Glu Thr Leu
                515                 520                 525
Glu Ala Gly Asp Asn His Phe Val Cys Ser Cys Glu Leu Leu Ser Phe
            530                 535                 540
Thr Met Glu Thr Pro Ala Leu Ala Gln Ile Leu Val Asp Trp Pro Asp
545                 550                 555                 560
Ser Tyr Leu Cys Asp Ser Pro Arg Leu His Gly His Arg Leu Gln
                565                 570                 575
Asp Ala Arg Pro Ser Val Leu Glu Cys His Gln Ala Leu Val Ser
                580                 585                 590
Gly Val Cys Cys Ala Leu Leu Leu Ile Leu Leu Val Gly Ala Leu
                595                 600                 605
Cys His His Phe His Gly Leu Trp Tyr Leu Arg Met Met Trp Ala Trp
    610                 615                 620
Leu Gln Ala Lys Arg Lys Pro Lys Lys Ala Pro Cys Arg Asp Val Cys
625                 630                 635                 640
Tyr Asp Ala Phe Val Ser Tyr Ser Glu Gln Asp Ser His Trp Val Glu
                645                 650                 655
Asn Leu Met Val Gln Gln Leu Glu Asn Ser Asp Pro Pro Phe Lys Leu
                    660                 665                 670
Cys Leu His Lys Arg Asp Phe Val Pro Gly Lys Trp Ile Ile Asp Asn
                675                 680                 685
Ile Ile Asp Ser Ile Glu Lys Ser His Lys Thr Val Phe Val Leu Ser
            690                 695                 700
Glu Asn Phe Val Arg Ser Glu Trp Cys Lys Tyr Glu Leu Asp Phe Ser
705                 710                 715                 720
His Phe Arg Leu Phe Asp Glu Asn Asn Asp Ala Ala Ile Leu Val Leu
                725                 730                 735
Leu Glu Pro Ile Glu Arg Lys Ala Ile Pro Gln Arg Phe Cys Lys Leu
                    740                 745                 750
Arg Lys Ile Met Asn Thr Lys Thr Tyr Leu Glu Trp Pro Leu Asp Glu
                755                 760                 765
Gly Gln Gln Glu Val Phe Trp Val Asn Leu Arg Thr Ala Ile Lys Ser
            770                 775                 780

<210> SEQ ID NO 3
<211> LENGTH: 586
<212> TYPE: PRT
<213> ORGANISM: Homo sapiens
```

<400> SEQUENCE: 3

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

```
Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
    450                 455                 460

Ser Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
            515                 520                 525

Glu Ala Gly Gly Asn Asn Phe Ile Cys Ser Cys Glu Phe Leu Ser Phe
            530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His
            580                 585

<210> SEQ ID NO 4
<211> LENGTH: 21
<212> TYPE: PRT
<213> ORGANISM: Homo sapiens

<400> SEQUENCE: 4

Lys Glu Glu Ser Ser Asn Gln Ala Ser Leu Ser Cys Asp Arg Asn Gly
1               5                   10                  15

Ile Cys Lys Gly Ser
            20

<210> SEQ ID NO 5
<211> LENGTH: 13
<212> TYPE: PRT
<213> ORGANISM: Homo sapiens

<400> SEQUENCE: 5

Cys Ser Cys Glu Phe Leu Ser Phe Thr Gln Glu Gln Gln
1               5                   10
```